United States Patent
Singh et al.

(10) Patent No.: US 6,316,493 B1
(45) Date of Patent: Nov. 13, 2001

(54) SUBSTITUTED 1,2,4-TRIOXANES AS ANTIMALARIAL AGENTS AND A PROCESS OF PRODUCING THE SUBSTITUTED 1,2,4-TRIOXANES

(75) Inventors: Chandan Singh; Sunil Kumar Puri, both of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/539,574

(22) Filed: Mar. 31, 2000

(30) Foreign Application Priority Data

Dec. 28, 1999 (IN) .............................. 1579/DEL/99

(51) Int. Cl.⁷ ....................... A61K 31/335; C07D 323/06
(52) U.S. Cl. ............................ 514/452; 549/368
(58) Field of Search ................. 514/452; 549/368

(56) References Cited

U.S. PATENT DOCUMENTS

| | | | |
|---|---|---|---|
| 5,225,437 | * 7/1993 | Posner et al. | 514/450 |
| 5,817,692 | * 10/1998 | Posner | 514/450 |
| 5,932,591 | * 8/1999 | Posner et al. | 514/314 |
| 6,136,847 | * 10/2000 | Posner et al. | 514/450 |
| 6,166,065 | * 12/2000 | Bachi et al. | 514/452 |

OTHER PUBLICATIONS

Singh et al, Synthesis of in vivo potent antimalarial 1,2,4–trioxanes, Chem. Abs. No. 119:139191, 1993.*

* cited by examiner

Primary Examiner—Deborah C. Lambkin
(74) Attorney, Agent, or Firm—Morgan & Finnegan

(57) ABSTRACT

The present invention relates to novel substituted 1,2,4-trioxanes that are useful as anti-malarial agents, and have a general formula 1,

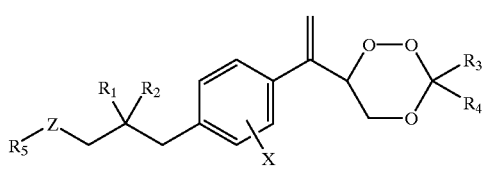

wherein $R_1$ and $R_2$ are selected from the group consisting of a hydrogen, a $C_{1-11}$ alkyl group; $R_3$ and $R_4$ are selected from the group consisting of a hydrogen, a $C_{1-11}$ alkyl group, a $C_{3-10}$ aryl group, a $C_{1-2}CO_2H$ carboxyalkyl group; and X represents hydrogen or a lower alkoxy group having 1 to 6 carbons.

30 Claims, 6 Drawing Sheets

9

10

11

12

13

14

15

16

17

18

19

20

21

22a

22b

23

24

25

26

27

28

29

30

31

32

33

34

35

36

Figure 1:
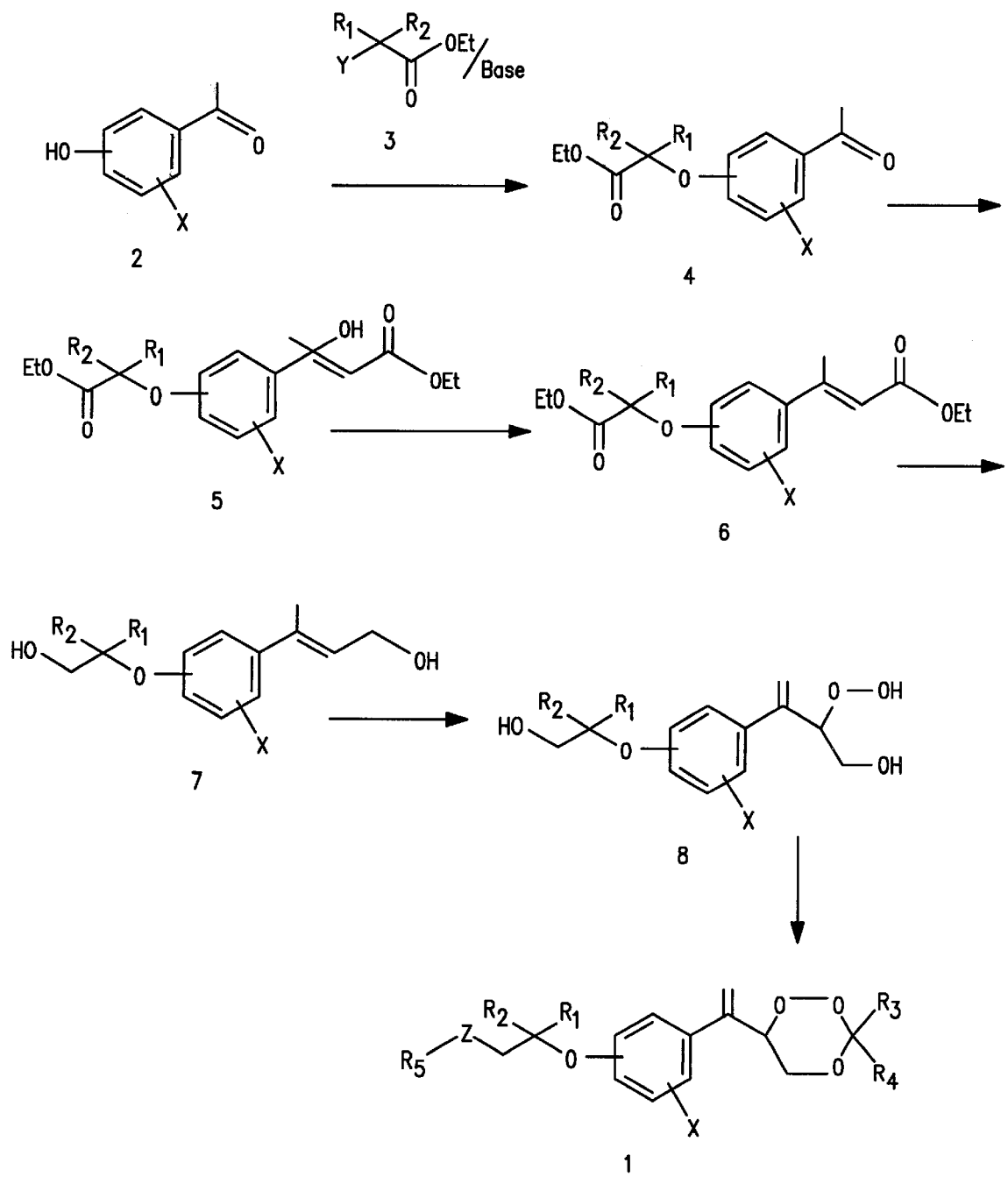
Figure 2A:
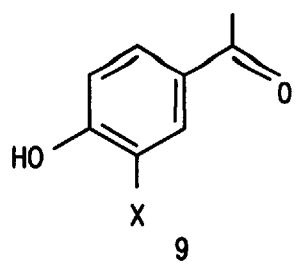
Figure 2A:
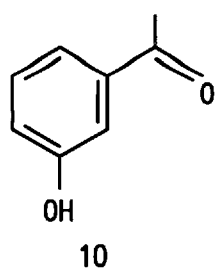
Figure 2A:
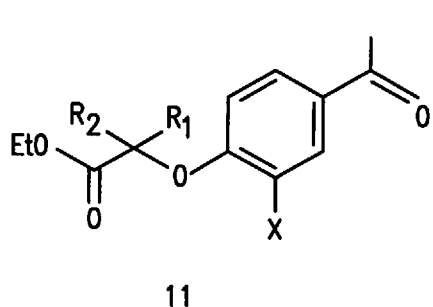
Figure 2A:
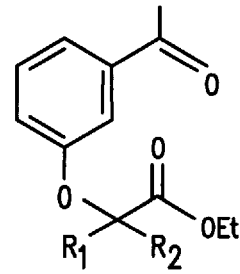
Figure 2A:
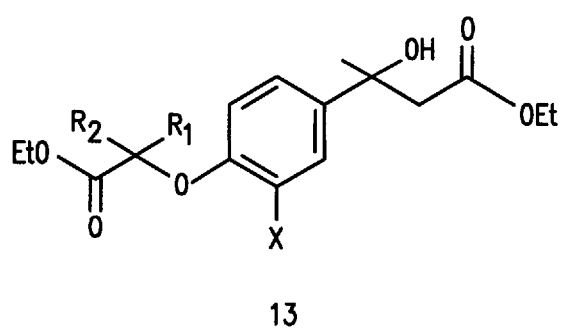
Figure 2A:
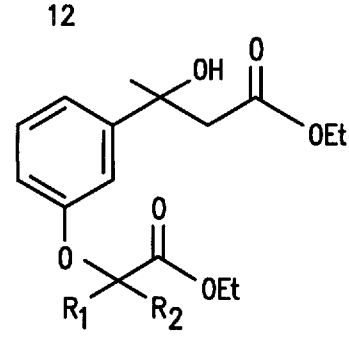
Figure 2A:
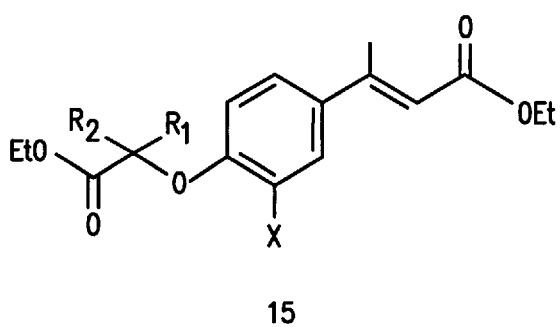
Figure 2A:
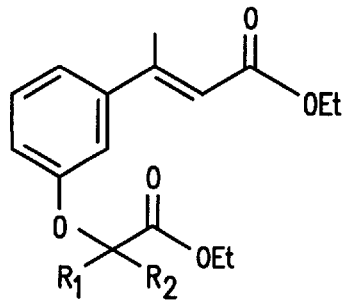
Figure 2B:
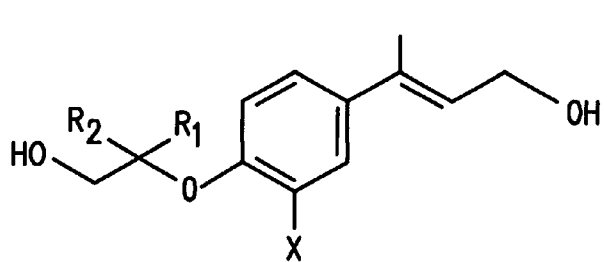
Figure 2B:
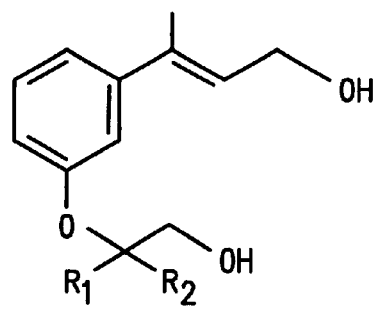
Figure 2B:
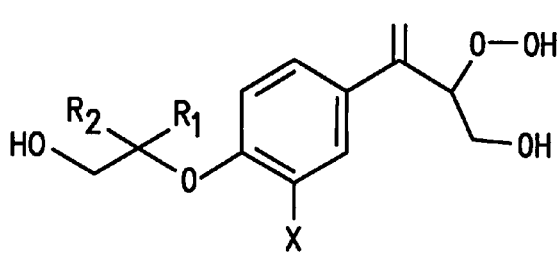
Figure 2B:
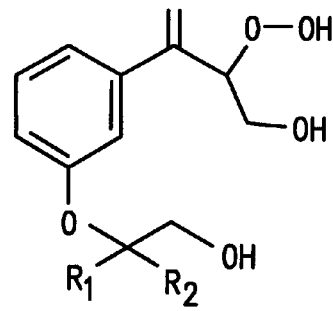
Figure 2B:
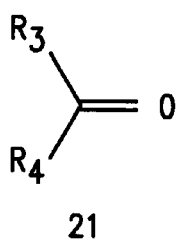
Figure 2B:
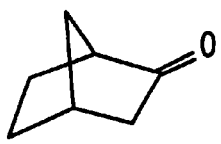
Figure 2B:
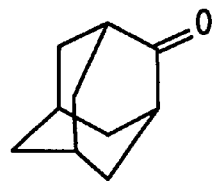
Figure 2C:
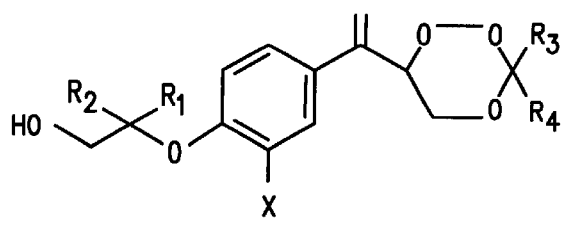
Figure 2C:
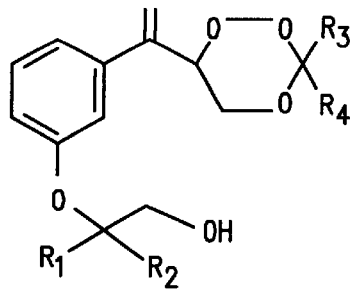
Figure 2C:
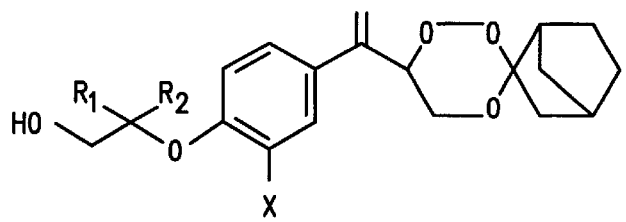
Figure 2C:
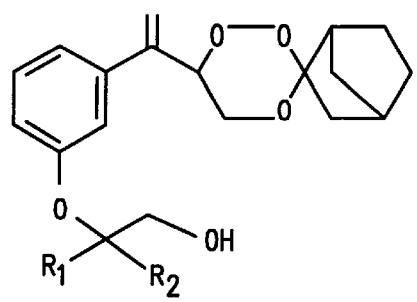
Figure 2C:
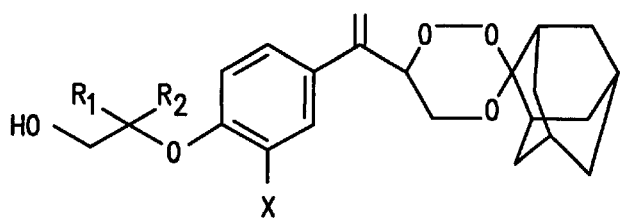
Figure 2C:
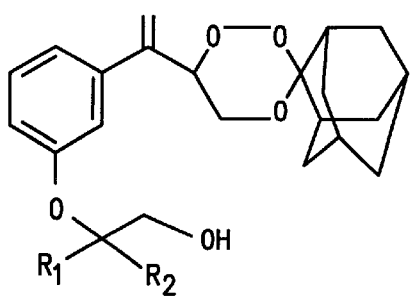
Figure 2D:
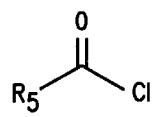
Figure 2D:
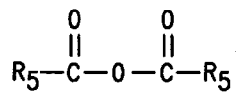
Figure 2D:
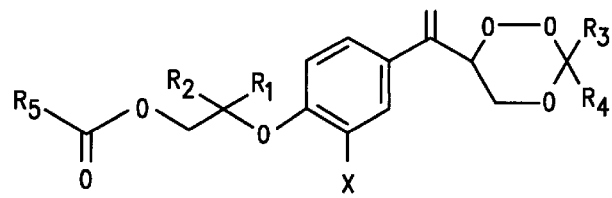
Figure 2D:
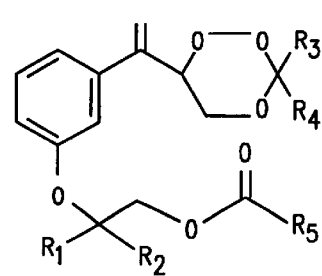
Figure 2D:
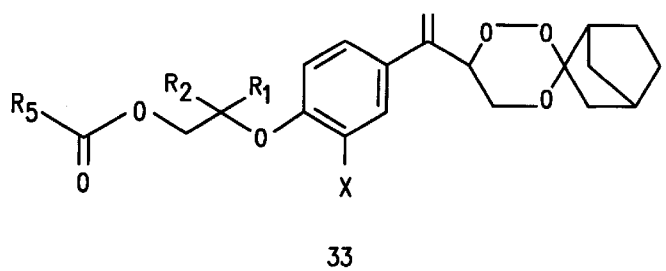
Figure 2D:
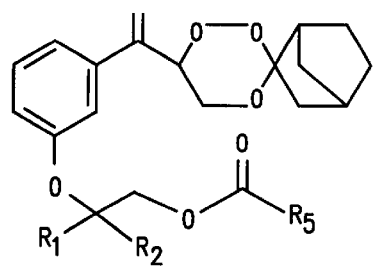
Figure 2D:
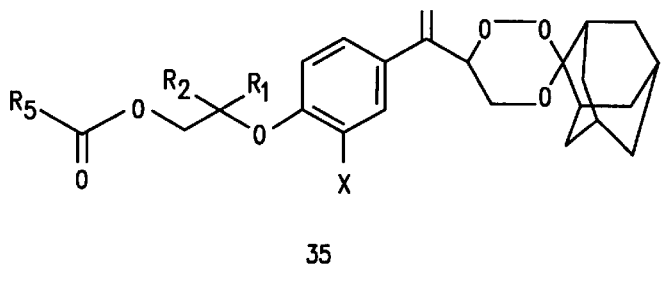
Figure 2D:
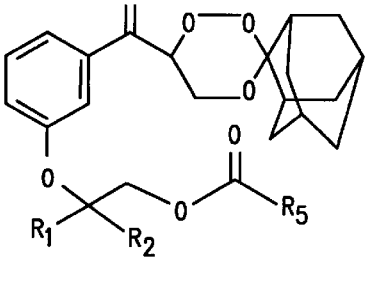
Figure 2E:
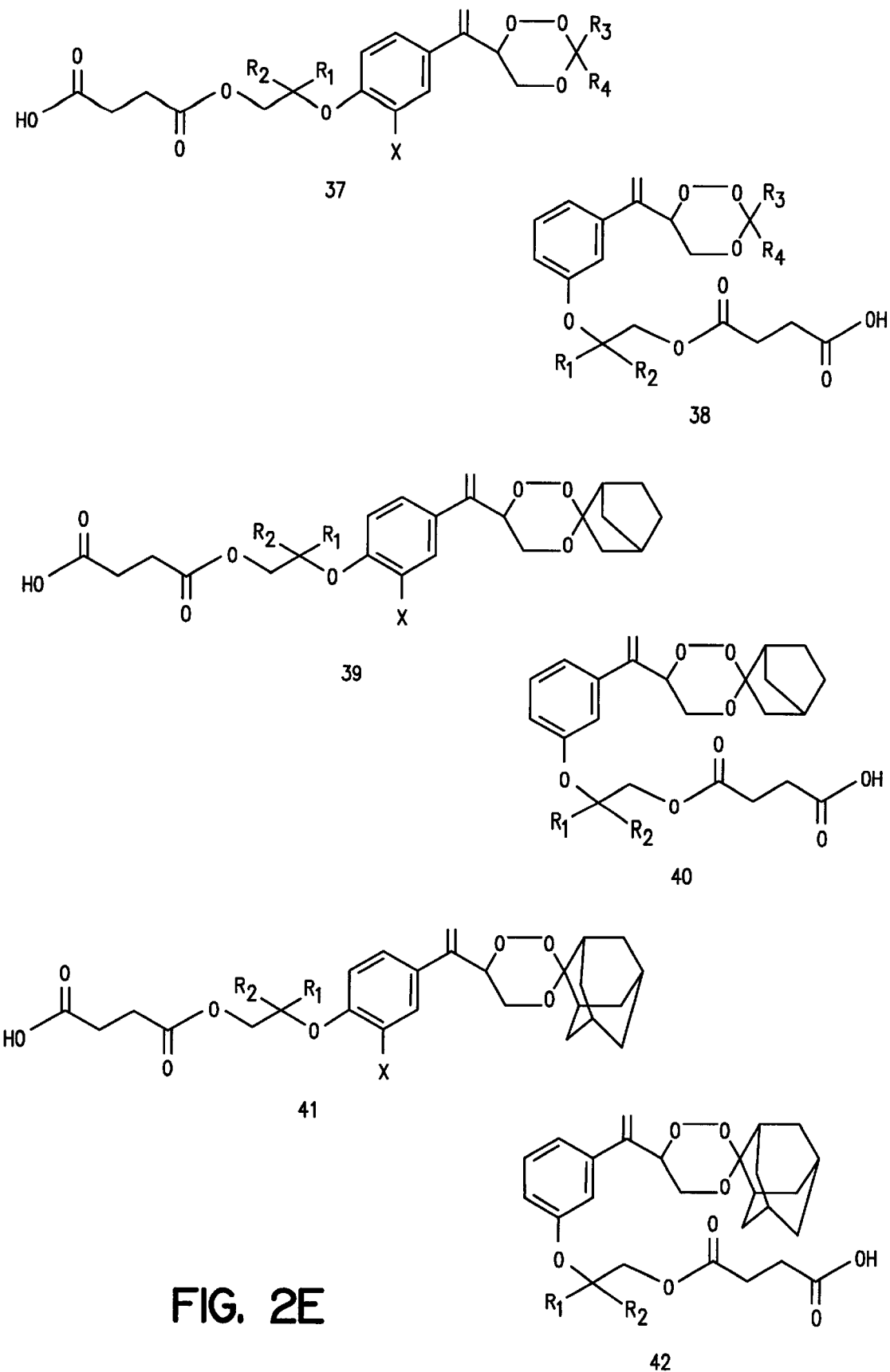

SUBSTITUTED 1,2,4-TRIOXANES AS ANTIMALARIAL AGENTS AND A PROCESS OF PRODUCING THE SUBSTITUTED 1,2,4-TRIOXANES

FIELD OF THE INVENTION

The present invention relates to novel substituted 1,2,4-trioxanes useful as anti-malarial agents. The invention also relates to a process for the preparation of novel substituted 1,2,4-trioxanes. More particularly, the invention relates to a process for the preparation of 6-[(α-(hydroxyalkoxy substituted aryl)vinyl-1,2,4-trioxanes and their esters useful as novel anti-malarial agents.

BACKGROUND OF THE INVENTION

Malaria is a killer disease in tropical countries. It is caused by Plasmodium. The four species of Plasmodium that infect human beings are *P. vivax, P. malariae, P. ovale* and *P. falciparium*. Some of the species that infect animals are *P. yoelii* in mice and *P. cynomolgi* in monkeys. These species cause severe complications in the patient that cause the patient to lapse into a coma and ultimately leads to death. In many parts of the world, there are several strains of Plasmodium that are resistant to drugs such as chloroquinone, mefloquine, halofantrine, quinine, etc. More than 270 million people suffer from the disease and more than 1.2 to 1.7 million die every year. Mortality among children under the age of 5 is common because such children are sensitive on account of their lack of immunity to the disease.

The need of the hour therefore is to develop novel anti-malarial drugs that can counter drug-resistant malarial infections.

OBJECTS OF THE INVENTION

The main objective of the invention is to provide novel substituted 1,2,4-trioxanes useful as anti-malarial agents.

Another objective of the present invention is to provide novel intermediate compounds also capable of being used as anti-malarial agents.

Yet another objective of the present invention is to provide a process for the preparation of hydroxy-functionalized thoxanes and their esters of general formula 1, a new series of anti-malarial agents.

Still another object is to provide a process for the preparation of intermediate compounds that exhibit anti-malarial properties.

DETAILED DESCRIPTION OF THE INVENTION

Accordingly, the invention provides novel substituted 1,2,4-trioxanes useful as anti-malarial agents. The invention also provides a process for the preparation of hydroxy-functionalized trioxanes and their esters having general formula 1, wherein $R_1$ and $R_2$ represent a hydrogen, an alkyl group such as methyl, ethyl, propyl; $R_3$ and $R_4$ represent a hydrogen, an alkyl group such as methyl, ethyl, an aryl such as phenyl, naphthyl or part of a cyclic system; $R_5$ represents hydrogen, alkyl group such as methyl, ethyl, propyl, aryl such as phenyl or a carboxy alkyl group such as $CH_2CH_2CO_2H$; X represents hydrogen or lower alkoxy such as OMe,

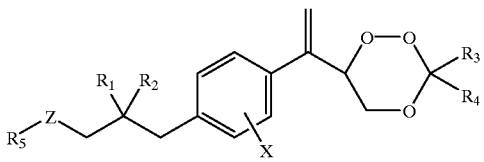

Z represents O or OCO. These compounds have been tested against multi-drug resistant *P. yoelii* in mice and several of them show promising anti-malarial activity. Some of these compounds with promising anti-malarial activity have been tested against *P. cynomolgi* in monkeys and have been found effective. The invention thus relates to the pharmaceutical industry. The trioxanes of general formula 1 are new chemical entities and they have not been prepared earlier. Trioxanes of general formula 1 are oil-soluble and can be administered as solution in oil such as groundnut oil. Some of the compounds of formula 1 are hemisuccinate derivatives and are soluble both in oil and aqueous $NaHCO_3$ solution and can be administered as a solution in groundnut oil or aqueous $NaHCO_3$. The mode of administration can be oral, intra-muscular, subcutaneous or intravenous. The said compounds, the preferred compounds and the intermediate compounds are described herein below with reference to the accompanying drawings and examples which have been provided merely to illustrate the invention and should not be construed as limitations on the inventive concept.

BRIEF DESCRIPTION OF THE ACCOMPANYING DRAWINGS

In the drawings that accompany,

FIG. 1 represents the sequence of the process of the invention wherein compound of formula 2 is converted to compound having formula 1.

FIG. 2 represents in series the structures of compounds 9 to 42, wherein FIG. 2(*a*) represents the structural formulae of compounds 9 to 16. FIG. 2(*b*) represents the structural formulae of compounds 17, 18, 19, 20, 21, 22a and 22b. FIG. 2(*c*) represents the structural formulae of compounds 23, 24, 25, 26, 27 and 28. FIG. 2(*d*) represents the structural formulae of the compounds having formula 29 to 36. FIG. 2(*e*) represents the structural formulae of the compounds having formula 37 to 42.

Formula 2 shown in FIG. 1 includes compounds of structural formulae 9 and 10 of the drawings. Formula 4 shown in FIG. 1 includes compounds of structural formulae 11 and 12 of the drawings. Formula 5 shown in FIG. 1 includes compounds of structural formulae 13 and 14 of the drawings. Formula 6 shown in FIG. 1 includes compounds of structural formulae 15 and 16 of the drawings. Formula 7 shown in FIG. 1 includes compounds of structural formulae 17 and 18 of the drawings. Formula 8 shown in FIG. 1 includes compounds of structural formulae 19 and 20 of the drawings. Formula 1 shown in FIG. 1 includes compounds of structural formulae 23 to 42 of the drawings.

Similarly, in FIG. 2(*a*), the compounds 11 to 16 are intermediate compounds.

Accordingly, the present invention provides a process for the preparation of novel substituted 1,2,4-trioxanes and their esters of general formula 1 which comprises reacting hydroxyacetophenones of formula 2 wherein X represents hydrogen or lower alkoxy such as OMe, with α-haloesters of formula 3 wherein $R_1$ and $R_2$ represent hydrogen, alkyl group such as methyl, ethyl, propyl and Y represents halogen such as Cl or Br, in the presence of a base optionally in an organic solvent at a temperature in the range of room temperature to refluxing temperature to give ketoesters of general formula 4, wherein $R_1$, $R_2$ and X have the same meaning as above; reacting ketoesters of general formula 4 under Reformatsky condition in an aprotic organic solvent in the temperature range of room temperature to refluxing temperature to give β-hydroxyesters of general formula 5, wherein $R_1$, $R_2$ and X have the same meaning as above; dehydrating β-hydroxyesters of formula 5 using a catalyst in an organic solvent at a temperature in the range of room temperature to refluxing temperature to give α,β-unsaturated esters of general formula 6, wherein $R_1$, $R_2$ and X have the same meaning as above; reducing α,β-unsaturated esters of general formula 6 with a complex metal hydride such as $LiAlH_4$ in an ether solvent at a temperature in the range of 0° C. to room temperature to give allylic alcohols of formula 7 wherein $R_1$, $R_2$ and X have the same meaning as above; oxygenation of allylic alcohols of formula 7 in the presence of a sensitizer in an organic solvent at a temperature in the range of −10° C. to room temperature to give β-hydroxyhydroperoxides of general formula 8 wherein $R_1$, $R_2$ and X have the same meaning as above; isolating and then reacting or reacting in situ β-hydroxyhydroperoxides of formula 8 with compounds containing aldehyde or ketone group in the presence of an acid catalyst in an organic solvent at a temperature in the range of 0° C. to room temperature to give hydroxy-functionalized 1,2,4-trioxanes of general formula 1, wherein $R_1$, $R_2$ and X have the same meaning as above, $R_3$ and $R_4$ are hydrogen, alkyl group such as methyl, propyl, aryl group such as phenyl, naphthyl or part of a cyclic system, $R_5$ is H and Z is O; reacting hydroxy-functionalized trioxanes of general formula 1, wherein $R_5$ is H and Z is O with an acid chloride or anhydrides in the presence of a base in an organic solvent at a temperature in the range of 0° C. to room temperature to give trioxane esters of general formula 1, wherein $R_1$, $R_2$, $R_3$, $R_4$ and X have the same meaning as above, $R_5$ is alkyl group such as methyl, ethyl, propyl, aryl group such as phenyl, carboxyalkyl such as $CH_2CH_2CO_2H$; and Z is OCO.

In the process hydroxyacetophenones of formula 2 are reacted with α-haloesters of formula 3 in the presence of a base such as $Na_2CO_3$, $K_2CO_3$, $KHCO_3$ in an organic solvent such as acetone, dimethylformamide, dimethylsulfoxide or without solvent, to give ketoesters of general formula 4. These ketoesters can be isolated and purified by standard laboratory methods such as crystallization or chromatography using an adsorbent such as silica gel. All ketoesters of general formula 4 except 11a (formula 11, $R_1=R_2=X=H$), 11c (formula 11, $R_1=H$, $R_2=Me$, X=H) and 12a (formula 12, $R_1=R_2=H$) are new compounds and they have not been prepared earlier. Ketoesters 11a, 11c and 12a are known compounds. [(a) *Chim. Ther.*, 8, 574 (1973), *Indian J. Chem.*, 24, 119 (1985), *Chem. Abstracts*, 124, 8616e (1996)].

In the process ketoesters of general formula 4 are reacted with ethyl bromoacetate and Zn in an aprotic solvent such as benzene, diethyl ether, to give β-hydroxyesters of general formula 5. These β-hydroxyesters can be isolated and purified by standard laboratory methods such as column chromatography using an adsorbent such as silica gel and a hydrocarbon solvent in combination with ethyl acetate as eluant or can be used without purification in the next step. β-hydroxyesters of general formula 5 are new compounds and they have not been prepared earlier. These hydroxyesters of general formula 5 have an additional ester group as part of substitution in the aromatic ring.

In the process dehydration of β-hydroxyesters of general formula 5 is accomplished in an hydrocarbon solvent such as benzene, toluene, $CH_2Cl_2$, in the presence of a catalyst such as $I_2$, p-toluene-sulfonic acid, $P_2O_5$, or acidic resin such as Amberlyst-15 to give α,β-unsaturated esters of general formula 6. These unsaturated esters can be isolated and purified by standard laboratory methods such as chromatography using an adsorbent such as silica gel. α,β-Unsaturated esters of general formula 6 have an additional ester group as part of substitution in the aromatic ring. These esters of general formula 6 are new compounds and they have not been prepared earlier.

In the process reduction of α,β-unsaturated esters of general formula 6 is done by reacting the compound with a complex metal hydride such as $LiAlH_4$ in an ether solvent such as diethyl ether, THF, to give allylic alcohols of general formula 7. These allylic alcohols of general formula 7 have an additional hydroxyl group as hydroxyalkoxy substitution in the aromatic ring. These allylic alcohols of general formula 7 can be isolated and purified by standard laboratory methods such as chromatography using an adsorbent such as silica gel and a hydrocarbon solvent in combination with ethyl acetate as eluant. Compounds of general formula 7 are new chemical entities and they have not been prepared earlier.

In the process allylic alcohols of general formula 7 are converted to β-hydroxyhydroperoxides of formula 8 by passing oxygen gas in the solution of the alcohol in an organic solvent and in the presence of a dye and a light source which provides visible light. The dye which acts as a sensitizer, i.e. converts triplet oxygen to highly reactive singlet oxygen, may be such as methylene blue, Rose Bengal, and tetraphenylporphine. Organic solvent used may be such as $CH_2Cl_2$, $CH_3CN$, acetone, methanol, and benzene. These β-hydroxyhydroperoxides of general formula 8 can be isolated and purified by known laboratory methods or can be used in situ, without purification and isolation, in the next step. These β-hydroxyhydroperoxides of formula 8 are new chemical entities and they have not been prepared earlier. Furthermore, these β-hydroxyhydroperoxides have an extra hydroxyl group in the form of hydroxyalkoxy substitution in the aromatic ring. The novel feature of these β-hydroxyhydroperoxides is that this extra hydroxyl group which is present as a hydroxyalkoxy substituent in the aromatic ring, does not take part in the next reaction, i.e. condensation of hydroperoxides with aldehyde and ketones and thus provide 1,2,4-trioxanes which carry a hydroxy group suitable for further derivatization.

In the process β-hydroxyhydroperoxides of general formula 8 are converted to hydroxy-functionalized 1,2,4-trioxanes of general formula 1 ($R_5=H$, Z=O) by reacting these hydroperoxides with carbonyl compounds of formulae 21–22 in the presence of an acid catalyst in an aprotic organic solvent. The carbonyl compounds used may be such as benzaldehyde, naphthaldehyde, acetone, ethyl methyl ketone, methyl propyl ketone, methyl isobutyl ketone, 4-heptanone, 5-nonanone, 6-undecanone, dibenzyl ketone and cyclic ketones such as cyclopentanone, cyclohexanone, cycloheptanone, bicyclic ketone such as norcomphor (22a) and tricyclic ketone such as 2-adamantanone (22b). The acid catalyst used may be HCl, $H_2SO_4$, p-toluene-sulfonic acid, $BF_3.OEt_2$, acidic resin such as Amberlyst-15. The organic solvent used may be $CH_2Cl_2$, $CHCl_3$, benzene, or $CH_3CN$. These trioxanes of general formula 1 ($R_5=H$, Z=O) are stable compounds and can be isolated and purified by standard chromatographic techniques using an adsorbent such as silica gel and a hydrocarbon solvent in combination with polar organic solvent as eluant. These trioxanes of general formula 1 ($R_5$=H, Z=O) are new chemical entities and they have not been prepared earlier. The novel feature of these trioxanes is that they are equipped with a primary hydroxyl group suitable for making derivatives of these trioxanes. This hydroxyl group is part of an alkoxy substituent in the aromatic ring. These trioxanes of general formula 1 ($R_5$=H, Z=O) have been tested against malarial parasites in animal models and several of them show very promising anti-malarial activity, both against chloroquine sensitive and chloroquine resistant malaria. These trioxanes are oil-soluble and can be administered as solution in oil such as groundnut oil. Some of these trioxanes have shown significant gamatocidal activity.

In the process, reaction of trioxanes of general formula 1 ($R_5$=H, Z=O) with acid chlorides of formula 29 or acid anhydrides of formula 30 wherein $R_5$ is an alkyl group such as methyl, ethyl, propyl, or an aryl group such as phenyl, is done in an aprotic organic solvent in the presence of a base to give trioxane esters of general formula 1 wherein $R_5$ is an alkyl group such as methyl, ethyl, propyl, or an aryl group such as phenyl, and Z is OCO. In the reaction, the hydroxyl group of trioxanes of formula 1 ($R_5$=H, Z=O) is esterified. The acid chlorides and acid anhydrides used may be acetyl chloride, benzoyl chloride, propionic anhydride, butyric anhydride, and/or heptanoic anhydride. The base can be such as $Et_3N$, pyridine, with or without a catalyst such as 4-dimethylaminopyridine (DMAP). The organic solvent used may be for example, $CH_2Cl_2$, $CHCl_3$, THF, or $CH_3CN$. These trioxanes of general formula 1 ($R_5$=alkyl, aryl, Z=OCO) can be isolated and purified by known laboratory methods such as crystallization or chromatography using an adsorbent such as silica gel and hydrocarbon solvent in combination with polar organic solvents as eluant. The trioxanes are new chemical entities that have not been prepared earlier. These trioxanes are oil-soluble and can be administered as solution in edible oil such as groundnut oil. Some of the trioxanes of general formula 1 ($R_5$=alkyl, aryl; Z=OCO) have shown promising anti-malarial activity in animal models.

In the process, trioxanes of formula 1 ($R_5$=H, Z=O) are reacted with succinic anhydride in an aprotic solvent in the presence of tertiary amine with or without the presence of 4-dimethylaminopyridine (DMAP) to give carboxy functionalized trioxanes of general formula 1 ($R_5$=$CH_2CH_2CO_2H$; Z=OCO). The tertiary amine may be for example, $Et_3N$ or pyridine. Aprotic organic solvents may be for example, $CH_2Cl_2$, $CHCl_3$, $CH_3CN$, toluene or THF. In the reaction, the hydroxyl group of the trioxanes of formula 1 ($R_5$=H, Z=O) is esterified. The trioxanes of general formula 1 ($R_5$=$CH_2CH_2CO_2H$; Z=OCO) have a carboxyl group and are soluble in aqueous bicarbonate or carbonate solutions. Thus they can be administered both as solution in oil or aqueous bicarbonate/carbonate solutions. Trioxanes of general formula 1 ($R_5$=$CH_2CH_2CO_2H$; Z=OCO) can be isolated and purified by known laboratory methods such as given above. Trioxanes of general formula 1 ($R_5$=$CH_2CH_2CO_2H$; Z=OCO) are new chemical entities that have not been prepared earlier. Some of these trioxanes have shown promising anti-malarial activity against both chloroquine-sensitive and resistant malaria in animal models. Some of these trioxanes also show significant gamatocidal activity.

The invention is further illustrated by the following examples, which should not, however, be construed to limit the scope of the present invention.

EXAMPLE 1

Ethyl (4-acetylphenoxy) acetate (compound 11a, formula 11, $R_1$=$R_2$=X=H)

A mixture of p-hydroxyacetophenone (50 g), ethyl chloroacetate (60 ml), $K_2CO_3$ (120 g) in acetone (450 ml) was refluxed with stirring for 24 h. The reaction mixture was filtered and the residue was washed with acetone. The combined filtrate was concentrated and the residue was redissolved in ether. The ether extract was washed with aqueous NaOH, and then with water, dried, concentrated and purified by chromatography on silica gel using hexane-ethylacetate as eluant to give 63.3 g (77% yield) of 11a, m.p.64–68° C.

Compound 11a was also prepared using the conditions as given in Table 1.

TABLE 1

| α-Haloesters | Solvent | Base | Temp. | Time | Yield (%) |
| --- | --- | --- | --- | --- | --- |
| Ethyl bromoacetate | DMF | $K_2CO_3$ | Room temp. | 5 h | 16 |
| Ethyl chloroacetate | DMSO | $K_2CO_3$ | Room temp. | 6 h | 68 |
| Ethyl bromoacetate | Neat | $K_2CO_3$ | Room temp. | 13 h | 61 |
| Ethyl chloroacetate | Neat | $KHCO_3$ | 120° C. | 7.5 h | 42 |
| Ethyl chloroacetate | Neat | $Na_2CO_3$ | 120° C. | 14 h | 9 |

β-Hydroxyesters 13a (formula 13, $R_1$=$R_2$=X=H)

To a mixture of ketoester 11a (20 g) zinc metal (12 g), $I_2$ (20 mg) in benzene was added ethyl bromoacetate (10 ml) dropwise. The reaction mixture was refluxed for another 7 hr, cooled, acidified with aqueous HCl. The benzene layer was separated and the aqueous layer was extracted with benzene. Combined organic extract was washed with water and then aqueous $NaHCO_3$, dried and concentrated. The crude product was purified by column chromatography on silica gel using a mixture of hexane and ethylacetate as eluant to furnish β-hydroxyester 13a (63% yield) as an oil.

Compound 13a was also prepared using the conditions given in Table 2.

TABLE 2

| α-Haloester | Solvent | Temp. | Time |
| --- | --- | --- | --- |
| Ethyl chloroacetate | Benzene | Reflux | 21 h used in the next step without purification |
| Ethyl bromoacetate | Ether | Room Temp. | 35 h used in the next step without purification |

α,β-Unsaturated ester 15a (formula 15, $R_1$=$R_2$=X=H)

A mixture of β-hydroxyester 13a (10 g) and $P_2O_5$ (4 g) in benzene (150 ml) was refluxed for 2.5 h. The reaction mixture was filtered and the filtrate was concentrated to give 10 g of crude product which was purified by column chromatography on silica gel using hexane-ethylacetate as eluant to give 5.13 g (56% yield) of α,β-unsaturated ester 15a as an oil.

Allylic alcohol 17a (formula 17, $R_1$=$R_2$=X=H)

To a stirred and ice-cooled mixture of $LiAlH_4$ (6 g) in dry ether (400 ml), a solution of α,β-unsaturated ester 15a (12 g) in ether was added dropwise. The reaction mixture was stirred in an ice-bath for 5 h. and then quenched with water and 10% NaOH. The organic layer was separated, dried on $Na_2SO_4$ and concentrated to give 8.84 g. of crude product which was purified by column chromatography to furnish 5.67 g (59%) of allylic alcohol 17a; m.p; 83–86° C.

3-[4-(2-Hydroxyethoxy)phenyl]-1-hydroxy-but-3-en-2-hydroperoxide (compound 19a, general formula 19, $R_1$=$R_2$=H, X=H)

(1) A solution of allylic alcohol 17a and methylene blue (15 mg) in ethanol (60 ml) was irradiated with a 250-watt tungsten-halogen lamp at −10° C. while a slow stream of oxygen was passed through the reaction mixture for 9.5 h. The reaction mixture was diluted with water and extracted with ether. The ether extract was concentrated and the crude product was chromatographed on silica gel using CH2Cl2—ether as eluant to give 650 mg (28% yield) of β-hydroxyhydroperoxide 19a.

(2) A solution of allylic alcohol 17a (1 g), tetraphenylporphine (50 mg) in $CHCl_3$ (60 ml) was photooxygenated at r.t. for 6 h. β-hydroxyhydroperoxide 19a separated as a solid. It was washed with ether to give 500 mg (44% yield) of TLC pure 19a.

Trioxane 23a1 (formula 23, $R_1=R_2=X=H$, $R_3$, $R_4=$—$CH_2CH_2CH_2CH_3$)

(1) Two-pot procedure: A mixture of β-hydroxyhydroperoxide 19a (900 mg), cyclopentanone (2 ml) and p-toluene sulfonic acid (50 mg) in acetonitrile (10 ml) was stirred at room temperature for 3.5 h. The reaction mixture was diluted with saturated aqueous $NaHCO_3$ and extracted with ether. The ether extract was concentrated and the crude product was purified by chromatography (elution with ethylacetate-hexane; 1:9) to furnish 310 mg (44% yield) of trioxane 23a1.

(2) One-pot procedure: A solution of alcohol 17a (3.5 g) and methylene blue (10 mg) in $CH_3CN$ (65 ml) was irradiated with a tungsten-halogen lamp at 0° C. for 7.5 h when a slow stream of oxygen was passed through the reaction mixture to give β-hydroxyhydroperoxide 19a as indicated by TLC. To the reaction mixture were added cyclopentanone (6 ml) and p-toluene sulfonic acid (50 mg) and the reaction mixture was stirred at r.t. for 2 days. Workup and purification by chromatography furnished 1.14 g (23% yield based on alcohol 17a) of trioxane 23a1.

Acetate of trioxane 23a1 (compound 31a1, formula 31, $R_1=R_2=H$; $R_3$, $R_4=CH_2CH_2CH_2CH_3$; $R_5=CH_3$; X=H)

A solution of trioxane 23a1 (200 mg) in pyridine (6 ml) was treated with acetic anhydride (0.5 ml) and the resulting mixture was left in the refrigerator (~5° C.) overnight. The reaction mixture was diluted with water and extracted with ether. Ether extract was washed sequentially with water, 10% HCl, water, and then dried ($Na_2SO_4$) and concentrated. The crude product was purified by column chromatography on silica gel to give 180 mg (91% yield) compound 31a1 as an oil

EXAMPLE 2
Benzoate of trioxane 23a1 (compound 31a5, formula 31, $R_1=R_2=H$; $R_3$, $R_4=CH_2CH_2CH_2CH_3$; $R_5=Ph$; X=H)

A solution of trioxane 23a1 (180 mg) and benzoyl chloride (0.5 ml) in pyridine (3 ml) was left at r.t. overnight. The reaction mixture was diluted with water and extracted with ether. Ether was extracted as usual processing followed by column chromatography on silica gel using hexane-ethylacetate as eluant and furnished 100 mg (42% yield) of benzoate 31a5 as an oil.

EXAMPLE 3
Trioxane 23a2 (formula 23, $R_1=R_2=X=H$, $R_3$, $R_4=$—$CH_2CH_2CH_2CH_2CH_3$)

A solution of allylic alcohol 17a (1 g) and methylene blue (15 mg) in acetonitrile was photooxygenated at 0° C. for 6.5 h. as above and then reacted with cyclohexanone (2 ml) using p-toluenesulfonic acid as catalyst at r.t. for 5 h. The crude product obtained after workup as above was purified by chromatography to give 0.86 g (57% yield based on the alcohol 17a) of 1,2,4-trioxane 23a2.

EXAMPLE 4
Trioxane 23a3 (formula 23, $R_1=R_2=X=H$; $R_3=R_4=Me$)

(1) From β-hydroxyhydroperoxide 19a. To a solution of β-hydroxyhydroperoxide 19a (100 mg) in acetone (5 ml) was added one drop of concentrated (conc.) HCl and the reaction mixture was stirred at r.t. for 30 minutes. The reaction mixture was concentrated under vacuum and the crude product was purified by chromatography on silica gel using hexane-ethylacetate as eluant to give 60 mg (52% yield) of trioxane 23a3.

(2) From allylic alcohol 17a. A solution of allylic alcohol 17a (1 g) and Rose Bengal (5 mg) in acetone (40 ml) was photooxygenated at −8° C. for 6 h. To this reaction mixture were added 3 drops of conc. HCl and the reaction mixture was left overnight at r.t. The solvent was removed under vacuum and the crude product was chromatographed on silica gel as above to furnish 340 mg (26% yield based on allylic alcohol 17a) of trioxane 23a3.

EXAMPLE 5
Trioxane 27a (formula 27, $R_1=R_2=X=H$)

A solution of allylic alcohol 17a (2 g) and methylene blue (5 mg) in $CH_3CN$ (60 ml) was photooxygenated at 0° C. for 6 h to give β-hydroxyhydroperoxide 19a as indicated by TLC. To this reaction mixture 2-adamantanone (2 g) was added and the reaction mixture was stirred for 1 h when p-toluenesulfonic acid (10 mg) was added and the reaction mixture was stirred for another 6 h at room temperature. The reaction was quenched with aqueous $NaHCO_3$, diluted with water and extracted with ether. Ether extract was washed with water, dried ($Na_2SO_4$) concentrated and the crude product was purified by chromatography on silica gel to furnish 1.9 g (57% yield based on alcohol 17a) of trioxane 27a as an oil.

Acetate of trioxane 27a (compound 35a1, formula 35, $R_1=R_2=H$; $R_5=CH_3$; X=H)

A mixture of trioxane 27a (200 mg), acetic anhydride (1 ml) in pyridine (4 ml) was left at r.t. overnight. The reaction mixture was diluted with water and extracted with ether. Ether extract was washed with water, 10% aqueous HCl, water, dried ($Na_2SO_4$) and concentrated to give 200 mg of crude product which was purified by chromatography on silica gel (8 g, elution with 50% EtOAc in $CH_2Cl_2$) to give 178 mg (80% yield) of acetate 35a1 as an oil.

Hemisuccinate of trioxane 27a (compound 41a, formula 41, $R_1=R_2=H$; X=H)

A mixture of trioxane 27a (2 g) and succinic anhydride (3 g) in pyridine (20 ml) was left at r.t. overnight. The reaction mixture was diluted with water and extracted with ether. The extract was washed with water, 10% HCl, water, dried ($Na_2SO_4$) and concentrated to give 2.3 g of crude product which was purified by chromatography on silica gel (25 g, eluted with 50% ether in $CH_2Cl_2$) to give 1.5 g (60% yield) of hemisuccinate 41a as a highly viscous material.

EXAMPLE 6
Trioxane 23a13 (formula 23, $R_1=R_2=X=H$; $R_3$, $R_4=H$, 1-naphthyl)

A solution of allylic alcohol 17a (1.0 g) and methylene blue (70 mg) in $CH_3CN$ (50 ml) was photooxygenated at −10 to 0° C. for 6 h. To one-half of this reaction mixture were added 1-naphthaldehyde (1 ml) and p-toluene sulfonic acid (20 mg) and the reaction mixture was kept at 5° C.

overnight. Usual workup followed by purification by chromatography furnished trioxane 17a13 in 32% yield.

Hemisuccinate of trioxane 23a13 compound 37a4, formula 37, $R_1=R_2=H$; $R_3$, $R_4=H$, 1-naphthyl; X=H To an ice-cooled mixture of 23a13 (120 mg) and succinic anhydride (200 mg) in $CH_2Cl_2$ (20 ml) were added triethylamine (0.2 ml) and 4-dimethylaminopyridine (30 mg) and the reaction mixture was left overnight at r.t. Workup as above followed by column chromatography in silica gel using $CH_2Cl_2$-ether as eluant furnished hemisuccinate 37a4 as an oil (100 mg; 67% yield).

EXAMPLE 7

Ethyl 2-(4-acetylphenoxy)isobutyrate (compound 11b Formula 11, $R_1=R_2=Me$; X=H)

A mixture of p-hydroxyacetophenone (14 g), ethyl 2-bromoisobutyrate (21 g) and $K_2CO_3$ (40 g) in acetone (260 ml) was refluxed with stirring for 19 h. The reaction mixture was diluted with water and extracted with benzene. Usual processing of the benzene extract furnished 10.5 g (41% yield) of ketoester 11b as an oil.

Compound 11b was also prepared using the conditions as given in Table 3.

TABLE 3

| αHaloester | Solvent | Base | Temp. | Time | Yield (%) |
| --- | --- | --- | --- | --- | --- |
| Ethyl 2-bromoisobutyrate | Isobutyl methyl ketone | $K_2CO_3$ | Reflux | 11 h | 30 |
| " | DMSO | $K_2CO_3$ | Room temp. | 21 h | 27 |
| " | DMSO | $K_2CO_3$ | 50–60° C. | 21 h | 22 |
| " | Neat | $K_2CO_3$ | 120° C. | 14 h | 49 |

β-Hydroxyester 13b (formula 13, $R_1=R_2=Me$, X=H)

To a refluxing, mixture of ketoester 11b (12 g), zinc (6 g), $I_2$ (70 mg) in benzene (200 ml), ethyl bromoacetate (7 ml) was added dropwise and the reaction mixture was refluxed for 7 hr. Work up and purification by chromatography on silica gel (hexane-EtOAc on eluant) furnished 45% yield of β-hydroxyester 13b.

α,β-Unsaturated ester 15b (formula 15, $R_1=R_2=Me$, X=X)

To a refluxing mixture of ketoester 11b (10.5 g), zinc (5 g), $I_2$ (40 mg) in benzene (200 ml), a solution of ethyl bromoacetate (5 ml) in benzene (50 ml) was added dropwise and the reaction mixture was refluxed for 7 h. The reaction mixture was cooled and acidified with 10% aqueous HCl. Benzene layer was separated and the aqueous layer was extracted with benzene (2×150 ml). The combined organic extract was washed with water and aqueous $NaHCO_3$ solution, dried ($Na_2SO_4$) and concentrated to give β-hydroxyester 13b which was used in the next without isolation and purification.

The crude 13b as obtained above was dissolved in benzene (200 ml). $I_2$ (50 mg) was added and the reaction mixture was refluxed for 1.75 h. The reaction mixture was cooled, washed with aqueous sodium thiosulphate and then with water, dried ($Na_2SO_4$) and concentrated. The crude product was purified by column chromatography to furnish 6.80 g (51% yield) of (α,β-unsaturated ester 15b Allylic alcohol 17b (formula 17, $R_1=R_2=Me$; X=H)

To a stirred and ice-cooled mixture of $LiAlH_4$ (5 g) in dry ether (450 ml), a solution of α,β-unsaturated ester 15b (6.2 g) in dry ether was added dropwise. The reaction mixture was stirred for 5 h. and then quenched with water and 10% aqueous NaOH. The organic layer was separated. The residue was washed with ether and the combined organic extract was dried ($Na_2SO_4$), concentrated and the crude product was purified to give 3.0 g (66% yield) of allylic alcohol 17b, as an oil.

3-[4-(2-Hydroxy-1,1-dimethyl-ethoxy)phenyl]-1-hydroxy-but-3-en-2-hydroperoxide (compound 19b, formula 19, $R_1=R_2=Me$, X=H)

A solution of allylic alcohol 17b (1.40 g) and methylene blue (100 mg) in $CH_3CN$ (45 ml) was irradiated with a 500 watt tungsten-halogen lamp at 0° C. for 5 h while a slow stream of oxygen was passed through the reaction mixture. The reaction mixture was concentrated to 20 ml and then diluted with water (20 ml) and extracted with ether (3×25 ml). The combined ether extract was washed with water, dried ($Na_2SO_4$), concentrated and purified by chromatography on silica gel to furnish 860 mg (61% yield) of β-hydroxyhydroperoxide 19b as an oil.

Trioxane 23b1 (formula 23, $R_1=R_2=Me$, X=H; $R_3$, $R_4$=—$CH_2CH_2CH_2CH_3$)

A solution of allylic alcohol 17b (680 mg) and methylene blue (15 mg) in $CH_3CN$ (60 ml) was photooxygenated at 0° C. for 3.25 h to give β-hydroxyhydroperoxide 19b as indicated by TLC. This reaction mixture was divided into two equal parts. To one part were added cyclopentanone (2 ml) and PTSA (25 mg) and stirred at r.t. for 2.75 h. Usual workup followed by chromatography on silica gel furnished 240 mg (63% yield based on allylic alcohol 17b) of trioxane 23b1.

Hemisuccinate of trioxane 23b1 (compound 37b 1, formula 37, $R_1=R_2=Me$; $R_3$, $R_4=CH_2CH_2CH_2CH_3$; X=H)

A solution trioxane 23b1 (1 g) in $CH_2Cl_2$ (40 ml) was reacted with succinic anhydride as above and the product was purified by chromatography as above to furnish 1.23 g (93% yield) of hemisuccinate 37b1.

EXAMPLE 8

Trioxane 23b2 (formula 23, $R_1=R_2=Me$, X=H; $R_3$, $R_4$=—$CH_2$—$(CH_2)_3$—$CH_3$)

To one half of the photooxygenated mixture from the above example were added cyclohexanone (2 ml) and PTSA (25 mg) and the reaction mixture was stirred at r.t. for 2.75 h. Normal workup followed by purification by column chromatography on a silica gel gave 230 mg (46% yield based on the allylic alcohol 17b used) of trioxane 23b2.

EXAMPLE 9

Trioxane 27b (formula 27, $R_1=R_2=Me$, X=H)

A mixture of allylic alcohol 17b (2.0 g) and methylene blue (100 mg) in $CH_3CN$ (60 ml) was photooxygenated at 0° C. for 6.5 h. To this reaction mixture were added 2-adamantanone (3.0 g) and p-toluenesulfonic acid (100 mg) and the reaction mixture was left at room temperature overnight. The reaction mixture was quenched with aqueous $NaHCO_3$ diluted with water and extracted with ether. The ether extract was washed with water, dried ($Na_2SO_4$) and concentrated. The crude product was purified by column chromatography on a silica gel and gave 1.61 g (59% yield based on allylic alcohol 17b) of 1,2,4-trioxane 27b, m.p. 100–102° C.

Trioxane 27b was obtained in 44% yield when the condensation with 2-adamantanone was done using Amberlyst-15 as catalyst.

Acetate of trioxane 27b (compound 35b1, formula 35, $R_1=R_2=Me$; $R_5=CH_3$; X=H)

A solution of trioxane 27b (200 mg) and acetic anhydride (1 ml) in pyridine (4 ml) was reacted at r.t. overnight. Workup as above followed by column chromatography on silica gel furnished 0.21 g of acetate 35b1 as a viscous material.

EXAMPLE 10
Propionate of trioxane 27b (compound 35b2, formula 35, $R_1=R_2=Me$; $R_5=Et$; $X=H$)

To an ice-cooled mixture of 27b (300 mg) and propionic anhydride (1.3 ml) in $CH_2Cl_2$ (10 ml) were added triethylamine (0.8 ml) and 4-dimethylaminopyridine (20 mg) and left overnight at r.t. Usual workup as above followed by column chromatography on silica gel furnished 310 mg (91% yield) of propionate 35b2 as a colourless oil.

EXAMPLE 11
Hexanoate of trioxane 27b (compound 35b4, formula 35, $R_1=R_2=Me$; $R_5=$n-pentyl; $X=H$)

A mixture of trioxane 27b (300 mg) and hexanoic anhydride (1 ml) in $CH_2Cl_2$ (15 ml) was reacted in the presence of triethylamine (0.5 ml) and 4-dimethylamino pyridine (20 mg) at r.t. for 1 h. Workup as above followed by column chromatography on silica gel furnished 330 mg (89% yield) of hexanoate 35b4 as an oil.

EXAMPLE 12
Hemisuccinate of trioxane 27b (compound 41b, formula 41, $R_1=R_2=Me$; $X=H$)

To a stirred and ice-cooled mixture of trioxane 27b (2.3 g) and succinic anhydride (2.5 g) in $CH_2Cl_2$ (100 ml) were added triethylamine (2.5 ml) and 4-dimethylamino pyridine (50 mg) and the reaction mixture was stirred at r.t. for 2h., concentrated under reduced pressure, acidified (50 ml of 10% HCl) and extracted with ether (3×150 ml). Ether extract was washed with water (3×100 ml), dried ($Na_2SO_4$) and concentrated under reduced pressure to give 3.1 g of crude material which was chromatographed on silica gel (50 g, eluted with 50% ether in hexane) to give 2.3 g solid which was crystallized from ether-hexane to give 1.91 g, (68% yield) of hemisuccinate 41b as white crystals, mp. 96–99° C.

Similar yields of 41b were obtained when the reaction was done in the absence of 4-dimethylaminopyridine.

EXAMPLE 13
Ketoester 11f (formula 11, $R_1=R_2=H$, $X=OMe$)

Compound 11f was prepared from 3-methoxy-4-hydroxyacetophenone (formula 9, $X=OMe$) in 84% yield following the procedure used for the preparation of compound 11a as given in example 1.

β-Hydroxyester 13f (formula 13, $R_1=R_2=H$; $X=OMe$)

To a refluxing mixture of ketoester 11f (21 g), zinc (6 g), and catalytic amount of iodine in benzene (400 ml) was added dropwise ethyl bromoacetate (15 ml) and the reaction mixture was refluxed for 8 hr. Work up and purification as given in example 1 furnished 20 g (71% yield) of β-Hydroxyester 13f.

α,β-Unsaturated ester 15f (formula 15, $R_1=R_2=H$; $X=OMe$)

β-Hydroxyester 13f (20 g) was dehydrated with $P_2O_5$ in refluxing benzene as above and the crude product was purified by column chromatography on silica gel to furnish 10.5 g (55%) of α,β-unsaturated ester 15f.

Allylic alcohol 17f (formula 17, R1=R2=H; $X=OMe$)

α,β-Unsaturated ester 15f (1.2 g) was reduced with $LiAlH_{4s}$(240 mg) in dry ether (25 ml) at 0° C. Work and purification was done according to the procedure as given above to give 260 mg (29% yield) of allylic alcohol 17f.

Trioxane 27f (formula 27, $R_1=R_2=H$; $X=OMe$)

A solution of allylic alcohol 17f (550 mg), adamantanone (540 mg) and methylene blue (15 mg) in $CH_3CN$ (40 ml) was photooxygenated as above for 6 h. to give β-hydroxyhydroperoxide 19f (formula 19, $R_1=R_2=H$; $X=OMe$) as indicated by TLC. To this reaction mixture was added p-toluenesulfonic acid (20 mg) and was left at room temperature overnight. Workup as above followed by chromatography on silica gel furnished 180 mg (19% yield based on the allylic alcohol 17f used) of 1,2,3-trioxane 27f.

Hemisuccinate for trioxane 27f (compound 41f, formula 41, $R_1=R_2=H$; $X=OMe$)

Hemisuccinate 41f was prepared from trioxane 27f in 80% yield following the procedure used for preparation of compound 41a as given in Example 5.

EXAMPLE 14
Ketoester 11g (formula 11, $R_1=R_2=Me$; $X=OMe$)

A mixture of 4-hydroxy-3-methoxyacetophenone (15 g) ethyl 2-bromoisobutyrate (22 ml) and $K_2CO_3$ (45 g) in acetone (450 ml) was refluxed for 27 h. Most of the solvent was distilled off and the remainder was diluted with water and extracted with ether, ether extract dried on $Na_2SO_4$ and concentrated. The crude product was chromatographed on silica gel (elution with 5% ethylacetate in hexane) to furnish 4.41 g (18% yield) of ketoester 11g as an oil.

β-Hydroxyester 13g (formula 13, $R_1=R_2=Me$; $X=OMe$)

A mixture of ketoester 11g (4.4 g), zinc (3 g) and ethyl bromoacetate (2.5 g) in benzene was refluxed for 7 hr. Work up as above to give 6.0 g of crude product, which was used in the next step without purification.

α,β-Unsaturated ester 15g (formula 15, $R_1=R_2=Me$, $X=OMe$)

β-Hydroxyester 13g (crude product 6.0 g as obtained above) was dissolved in benzene (100 ml), $I_2$ (40 mg) was added the reaction mixture was refluxed for 6 hr. Workup and purification effected as above furnished 2.7 g (49% yield, based on ketoester 11g) of α,β-unsaturated ester 15g as an oil.

Allylic alcohol 17g, (formula 17, $R_1=R_2=Me$; $X=OMe$)

α,β-Unsaturated ester 15g (1.9 g) was reduced with $LiAlH_4$ (1.8 g) in dry ether at 0° C. as above. Normal workup followed by chromatography furnished 1.1 g (76% yield) of allylic alcohol 17g as an oil.

Trioxane 27g (formula 27, $R_1=R_2=Me$; $X=OMe$)

A solution of allylic alcohol 17g (1.1 g) and methylene blue (20 mg) in acetonitrile (50 ml) was photooxygenated as above at 0° C. for 7 h. to give β-hydroxyhydroperoxide 19g (formula 19, $R_1=R_2=Me$; $X=OMe$) as indicated by TLC. The reaction mixture was divided into two equal parts. One part was reacted with 2-adamantanone (500 mg) in the presence of conc. HCl (4 drops) at room temperature overnight. Usual workup followed by chromatography furnished 300 mg (34% yield based on the alcohol 17g used) of trioxane 27g as thick oil.

EXAMPLE 15
Trioxane 23g1 (formula 23, $R_1=R_2=Me$; $X=OMe$; $R_3$, $R_4=$—$CH_2CH_2CH_2CH_3$)

The other half of the reaction mixture as obtained in the above experiment was reacted with cyclopentanone (1 ml) in the presence of conc. HCl (5 drops) at r.t. overnight. Usual workup followed by purification furnished 2.10 m (28% yield based on alcohol 17g) of trioxane 23g1.

EXAMPLE 16
Ketoester 12a (formula 12, $R_1=R_2=H$)

A mixture of 3-hydroxyacetophenone (5 g), ethyl chloroacetate (5.6 ml) and $K_2CO_3$ (7.5 g) was heated at 65° C. with stirring for 13 h. It was cooled to room temperature, diluted with water (50 ml) and extracted with ether (2×100 ml). Ether extract was washed with water (3×50 ml), dried ($Na_2SO_4$), concentrated and chromatographed on silica gel using 50% ethylacetate-hexane as eluant to give 4.52 g (49% yield) of ketoester 12a as an oil.

α,β-Unsaturated ester 16a (formula 16, $R_1=R_2=H$)

To a refluxing mixture of ketoester 12a (15 g), zinc (6 g), iodine (70 mg) in benzene (350 ml), ethyl bromoacetate (8 ml) was added dropwise and the reaction mixture was refluxed for 9 hr. The reaction mixture was cooled, acidified with aqueous 10% HCl, benzene layer was separated and the aqueous layer was extracted with benzene. The combined benzene extract was washed with water, aqueous $NaHCO_3$, dried ($Na_2SO_4$) and concentrated to give 14a which was dehydrated with $P_2O_5$ (5 g) using the procedure as given in example 1, and the final product was purified by column chromatography on silica gel (hexane-ethylacetate as eluant) to furnish 14.75 g (45% based on 12a) of 16a as an oil.

Allylic alcohol 18a (formula 18, $R_1=R_2=H$)

To a stirred and ice-cooled mixture of $LiAlH_4$ (8 g) in dry ether (400 ml), a solution of α,β-unsaturated ester 16a (11 g) in dry ether was added dropwise and the reaction mixture was stirred in an ice bath for 6 h. It was quenched with $H_2O$ and 10% NaOH. The organic layer was separated and the residue was washed with ether. The combined ether extract was dried ($Na_2SO_4$), concentrated and purified by column chromatography on silica gel using hexane-ethylacetate as eluant to give 5.8 g (74% yield) of allylic alcohol 18a.

Trioxane 24a1 (formula 24, $R_1=R_2=H$; $R_3$, $R_4=CH_2CH_2CH_2CH_3$)

A solution of allylic alcohol 18a (1.0 g) and Rose Bengal (5 mg) in acetonitrile (65 mg) was photooxygenated at 0° C. for 7 h. to give β-hydroxyhydroperoxide 20a (formula 20, $R_1=R_2=H$) as indicated by TLC. To this reaction mixture were added cyclopentanone (1.5 ml) and p-toluenesulfonic acid (15 mg) and the reaction mixture was stirred at room temperature for 4 h. Workup as above followed by column chromatography on silica gel furnished 600 mg (43% yield based on allylic alcohol 18a) of trioxane 24a1.

Hemisuccinate of trioxane 24a1 (compound 38a1, formula 38, $R_1=R_2=H$; $R_3=R_4=CH_2CH_2CH_2CH_3$)

A solution trioxane 24a1 (600 mg) and succinic anhydride (2.0 g) in pyridine (5 ml) was stirred at room temperature overnight. The reaction mixture was diluted with water and extracted with ether. The ether extract was washed with water, 10% aqueous HCl, water, dried ($Na_2SO_4$) and concentrated. The crude product purified by column chromatography on silica gel using $CH_2Cl_2$-ether as eluant furnished 780 mg (98% yield) of hemisuccinate 38a1.

EXAMPLE 17

Trioxane 28a (formula 28, $R_1=R_2=H$)

A solution of allylic alcohol 18a (1.0 g) and methylene blue (5 mg) in $CH_2Cl_2$ (65 mg) was photooxygenated as above at 0° C. for 10 h. To the reaction mixture, were added 2-adamantanone (1 g) and p-toluenesulfonic acid (15 mg) and the reaction mixture was kept at room temperature overnight. Usual workup as above followed by purification by chromatography on silica gel column furnished 350 mg (21% yield based on allylic alcohol 18a) of trioxane 28a as a thick oil.

Hemisuccinate for trioxane 28a (compound 42a, formula 42, $R_1=R_2=H$)

Hemisuccinate 42a was prepared in 91% yield by reacting trioxane 28a with succinic anhydride following procedure as given in the above example.

EXAMPLE 18

Ketoester 12b (formula 12, $R_1=R_2=Me$)

A mixture of 3-hydroxyacetophenone (5 g) ethyl 2-bromoisobutyrate (5.4 ml) and $K_2CO_3$ (7.5 g) was heated at 120° C. for 6 h. The reaction mixture was diluted with water and extracted with ether. Ether extract was washed with water, dried, concentrated and chromatographed on silica gel to furnish 1.82 g (22% yield) of ketoester 12b as an oil.

α,β-Unsaturated ester 16b (formula 16, $R_1=R_2=Me$)

To a refluxing mixture of ketoester 12b (14.6 g), zinc (7.3 g) and iodine (50 mg) in benzene (400 ml), a solution of ethyl bromoacetate (7.3 ml) in benzene (50 ml) was added dropwise and the reaction mixture was refluxed for 14.5 hr., cooled, and acidified with 10% aqueous HCl. Benzene layer was separated, washed with aqueous $NaHCO_3$, dried and concentrated to give β-hydroxyester 14b, which was used in the next step without purification.

The crude β-hydroxyester 14b as obtained above was dissolved in benzene (500 ml), $P_2O_5$ (10 g) was added and the mixture was refluxed for 3 h. Usual workup followed by chromatography furnished α,β-unsaturated ester 16b (7 g, 42% yield based on 12b).

Allylic alcohol 18b (formula 18, $R_1=R_2=Me$)

To a stirred and ice-cooled mixture of $LiAlH_4$ (3.2 g) in dry ether (450 ml), a solution of α,β-unsaturated 16b (3.6 g) was added. The reaction mixture was stirred for 2.5 h. in an ice bath. It was quenched with water and 10% aqueous NaOH. The ether layer was separated and concentrated to give 2.6 g of residue which was chromatographed on silica gel to give 2.3 g (86% yield) of allylic alcohol 18b.

Trioxane 24b 1 (formula 24, $R_1=R_2=Me$; $R_3$, $R_4=CH_2CH_2CH_2CH_3$)

A mixture of allylic alcohol 18b (300 mg) and methylene blue (20 mg) in $CH_3CN$ (40 ml) was photooxygenated at 0° C. for 5.5 h. to give β-hydroxyhydroperoxide 20b (formula 20, $R_1=R_2=Me$) as indicated by TLC. The reaction mixture was divided in two equal parts. To one-half of this reaction were added cyclopentanone of (1 ml) and PTSA (40 mg) and the reaction mixture was stirred at room temperature for 5 h. Usual workup followed by chromatography on silica gel furnished 170 mg (81% yield based on alcohol 18b) of trioxane 24b 1.

Hemisuccinate for trioxane 24b1 (compound 38b1, formula 38, $R_1=R_2=Me$; $R_3$, $R_4=$—$CH_2CH_2CH_2CH_3$)

To an ice-cooled solution of trioxane 24b1 (200 mg) and succinc anhydride (400 mg) in $CH_2Cl_2$ (20 ml) were added $Et_3N$ (1 ml) and 4-dimethylamino-pyridine (DMAP, 20 mg) and the reaction mixture was stirred at room temperature for 1.5 h. The solvent was removed under vacuum, acidified with 10% aq.HCl and extracted with ether. Ether extract was washed with water, concentrated and purified by chromatography on silica gel to give 230 mg (92% yield) of compound 38b1 as an oil.

Trioxane 24b2 (formula 24, $=R_1R_2=Me$; $R_3$, $R_4=CH_2CH_2CH_2CH_3$)

To the other half of the photooxygenated mixture obtained as in the above experiment were added cyclohexanone (1 ml) and PTSA (40 mg) and the reaction mixture was stirred at r.t. for 5 h. Workup and chromatography on silica gel column as above furnished 110 mg (50% yield based on alcohol 18b) of trioxane 24b2.

Hemisuccinate for trioxane 24b2 (compound 38b2, formula 38, $R_1=R_2=Me$; $R_3$, $R_4=CH_2CH_2CH_2CH_2CH_3$)

Trioxane 24b2 (250 mg) was reacted with succinc anhydride (350 mg) in $CH_2Cl_2$ (20 ml) as above and the crude product was purified by chromatography on silica gel using 25% ether in $CH_2Cl_2$ as eluant to give 280 mg (87% yield) of compound 38b2 as an oil.

EXAMPLE 19

Trioxane 28b (formula 28, $R_1=R_2=Me$)

A solution of allylic alcohol 18b (300 mg) and methylene blue (70 mg) in $CH_3CN$ (30 ml) was photooxygenated at −8°

C. for 6 h. To the reaction mixture were added 2-adamantanone (300 mg) and p-toluenesulfonic acid (50 mg) and left at room temperature overnight. The solvent was removed under vacuum and the residue was diluted with aq. NaHCO$_3$ and water and extracted with ether. The ether extract was washed with water, dried, concentrated and chromatographed on silica gel to furnish 310 mg (62% yield) of trioxane 28b as an oil.

Hemisuccinate of trioxane 28b [compound 42b, formula 42, R$_1$=R$_2$=Me]

To a stirred ice-cooled mixture of trioxane 28b (100 mg) and succinic anhydride (200 mg) in CH$_2$Cl$_2$ (10 ml) were added triethylamine (0.5 ml) and 4-dimethylamino pyridine (20 mg) and the reaction mixture was stirred at r.t. for 3 h. The reaction mixture was concentrated under reduced pressure, acidified with 10% aqueous HCl and extracted with ether (2×20 ml). The ether extract was washed with water dried (Na$_2$SO$_4$), concentrated and purified by column chromatography on silica gel to give 100 mg (80% yield) of hemisuccinate 42b as a thick oil.

EXAMPLE 20

Ketoester 11c (formula 11, R$_1$=H, R$_2$=Me, X=H)

A mixture of 4-hydroxyacetophenone (5 g), ethyl 2-bromopropionate (5 ml) and K$_2$CO$_3$ (7.5 g) was heated at 120° C. for 7.5 h. The reaction mixture was extracted with ether, washed with water, dried, concentrated and chromatographed on silica gel to furnish 1.8 g (21% yield) of 11c, m.p. 64–72° C.

α,β-Unsaturated ester 15c (formula 15, R$_1$=H, R$_2$=Me, X=H)

To a refluxing mixture of ketoester 11c (25 g), Zn (6.5 g) and iodine (50 mg) in benzene (250 ml) was added dropwise ethyl bromoacetate (12 ml) and the reaction mixture was refluxed for 7 h. The crude product (13c) obtained after usual workup was dehydrated with iodine (2 g) in benzene (100 ml) by refluxing for 4 h. The reaction mixture was washed with a solution of sodium thiosulphate, concentrated and purified by chromatography on silica gel to give 14.6 g (47% yield) of 15c as an oil.

Allylic alcohol 17c (formula 17, R$_1$=H, R$_2$=Me, X=H)

α,β-Unsaturated ester 15c (5.0 g) was reduced with LiAlH$_4$ (3 g) in dry ether (250 ml) as above to give 2.7 g allylic alcohol 17c.

Trioxane 25c (formula 25, R$_1$=Me, R$_2$=X=H)

A solution of allylic alcohol 17c (1.5 g) and methylene blue (10 mg) in CH$_2$CN (45 ml) was photooxygenated as above for 6 h. to give β-hydroxyhydroperoxide 19c (formula 19, R$_1$=Me, R$_2$=X=H). One third (corresponding to 500 mg of 17c) was taken and reacted with norcomphor (1.0 g) in the presence of a catalytic amount of p-toluenesulfonic acid at r.t for 3 h. Usual workup followed by column chromatography on silica gel furnished 300 mg (38% yield based on the allylic alcohol 17c used) of trioxane 25c.

EXAMPLE 21

Ketoester 11d (formula 11, R$_1$=H, R$_2$=Et, X=H)

A mixture of 4-hydroxyacetophenone (5.0 g) ethyl 2-bromobutyrate (5 ml) and K$_2$CO$_3$ (7.5 g) was heated at 120° C. for 7.5 h. Workup followed by purification of the crude product as above (example 20) furnished 3.9 g (42% yield) of compound 11d as an oil.

α,β-Unsaturated ester 15d (formula 15, R$_1$=H, R$_2$=Et, X=H)

To a refluxing mixture of ketoester 11d (3.5 g), Zinc (2.0 g), iodine (50 mg) in benzene (50 ml), ethyl bromoacetate (1.5 ml) was added and the reaction mixture was refluxed for 5 h. It was acidified with 10% HCl, benzene layer was separated and concentrated and the crude product was purified by chromatography to give 2.45 g (52% yield) of 13d. Compound 13d (2.4 g) was dehydrated in refluxing benzene using P$_2$O$_5$ as catalyst. Workup followed by column chromatography on silica gel as above furnished 2.0 g (88% yield) of ester 15d as an oil.

Allylic alcohol 17d (formula 17, R$_1$=H; R$_2$=Et; X=H)

α,β-Unsaturated ester 15d (2.7 g) was reduced with LiAlH$_4$ (1.5 g) in dry ether (150 ml) and the crude product was purified by chromatography on silica gel using hexane-ethylacetate as eluant to give 1.2 g of allylic alcohol 17d.

Trioxane 27d (formula 27, R$_1$=Et, R$_2$=X=H)

A solution of allylic alcohol 17d (1.2 g) and methylene blue (10 mg) in CH$_3$CN (40 ml) was photooxygenated as above for 7 h. to give β-hydroxyhydroperoxide 19d (formula 19, R$_1$=Et, R$_2$=X=H) as indicated by TLC. To one half of this reaction mixture were added adamantanone (600 mg) and PTSA (10 mg) and the reaction mixture was stirred at r.t. for 2 h. Usual workup followed by chromatography on silica gel furnished 300 mg (30% yield based on the allylic alcohol 17d used) of trioxane 27d as oil.

EXAMPLE 22

Ketoester 11e (formula 11, R$_1$=H, R$_2$=n-pentyl, X=H)

A mixture of 4-hydroxyacetophenone (5.0 g) ethyl 2-bromoheptanoate (8.3 g) and K$_2$CO$_3$ was heated at 120° C. for 7.5 h. The reaction mixture was extracted with ether. Ether extract was washed with water, dried, concentrated and chromatographed on silica gel to furnish 9.1 g (89% yield) of compound 11e, as an oil.

α,β-Unsaturated ester 15e (formula 15, R$_1$=H, R$_2$=n-pentyl, X=H)

To a refluxing mixture of ketoester 11e (25 g), Zn (7.5 g), iodine (100 mg) in benzene (450 ml), ethyl bromoacetate (9 ml) was added dropwise and the resulting mixture was refluxed for 5.5 h. It was acidified with 10% HCl, benzene layer was separated, washed with aq. NaHCO$_3$ solution, dried and concentrated to give β-hydroxyester 13e which was used without purification in the next step.

Crude product 13e as obtained above was dissolved in benzene (350 ml), iodine (100 mg) was added and the mixture was refluxed for 2.5 h. The reaction mixture was washed with a solution of sodium thiosulphate, dried, concentrated and chromatographed on silica gel (elution with 5% ethyl acetate-hexane) to give 22.1 g (71% yield) of α,β-unsaturated ester 15e as an oil.

Allylic alcohol 17e (formula 17, R$_1$=H; R$_2$=n-pentyl; X=H)

α,β-Unsaturated ester 15e (12 g) was reduced with LiAlH$_4$ (10 g) in dry ether (600 ml) at 0° C. as above to give 8.3 g of crude product which was purified by chromatography on silica gel to furnish 6.5 g (71% yield) of allylic alcohol 17e.

Trioxane 23e1 (formula 23, R$_1$=CH$_2$CH$_2$CH$_2$CH$_2$CH$_3$; R$_2$=X=H; R$_3$, R$_4$=—CH$_2$CH$_2$CH$_2$CH$_3$)

A solution of alcohol 17e (2 g) and methylene blue (100 mg) in CH$_3$CN (60 ml) was photooxygenated at 0° C. for 4.5 h. to give β-hydroxyhydroperoxide 19e (formula 19, R$_1$=CH$_2$CH$_2$CH$_2$CH$_2$CH$_3$; R$_2$=X=H) as indicated by TLC. One half of this photooxygenated reaction mixture was reacted with cyclopentanone (2 ml) in the presence of PTSA (50 mg) at r.t. for 5.5 h. Usual workup and column chromatography on silica gel furnished 610 mg (45% yield based on allylic alcohol 17e used) of trioxane 23e1.

Trioxane 27e (formula 27, R$_1$=CH$_2$CH$_2$CH$_2$CH$_2$CH$_3$; R$_2$=X=H)

To the other half of the photooxygenated mixture as obtained in the above example were added 2-adamantanone (1 g) and PTSA (50 mg) and the reaction mixture was stirred at r.t. for 5 h. Usual workup followed by column chromatography on silica gel using hexane-ethylacetate as eluant furnished 780 mg (76% yield based on allylic alcohol 17e used) of trioxane 27e as a thick oil.

Hemisuccinate of trioxane 27e (compound 41e, formula 41, $R_1$=H, $R_2$=n-pentyl; X=H)

To a stirred and ice-cooled mixture of trioxane 27e (200 mg) and succinic anhydride (200 mg) in $CH_2Cl_2$ (20 ml) were added triethylamine (0.5 ml) and 4-dimethylamino pyridine (20 mg) and the reaction mixture was stirred at r.t. for 1.5 h. Workup as above followed by purification by column chromatography on silica gel furnished 200 mg (82% yield) of hemisuccinate 41e as a colourless oil.

Using the above procedures, the following hydroxy-functionalized trioxane and their esters were also prepared Trioxane 23a4 (formula 23, $R_1$=$R_2$=X=H; $R_3$, $R_4$=Me, Et); 36% yield
Trioxane 23a5 (formula 23, $R_1$=$R_2$=X=H; $R_3$, $R_4$=Me, $CH_2CH_2CH_3$); 43% yield
Trioxane 23a6 (formula 23, $R_1$=$R_2$=X=H; $R_3$, $R_4$=Me, $CH_2CHMe_2$); 29% yield
Trioxane 23a7 (formula 23, $R_1$=$R_2$=X=H; $R_3$=$R_4$=n-propyl); 21% yield
Trioxane 23a8 (formula 23, $R_1$=$R_2$=X=H; $R_3$=$R_4$=n-butyl); 11% yield
Trioxane 23a9 (formula 23, $R_1$=$R_2$=X=H; $R_3$=$R_4$=n-pentyl); 16% yield
Trioxane 23a10 (formula 23, $R_1$=$R_2$=X=H; $R_3$, $R_4$=—$CH_2$($CH_2$)$_9$—$CH_3$); 16% yield
Trioxane 23a11 (formula 23, $R_1$=$R_2$=X=H; $R_3$, $R_4$=—$CH_2$—$CH_2$—CO—$CH_2$—$CH_3$); 6% yield
Trioxane 23a12 (formula 23, $R_1$=$R_2$=X=H; $R_3$, $R_4$=H, —$C_6H_5$); 45% yield
Trioxane 23a13 (formula 23, $R_1$=$R_2$=X=H; $R_3$, $R_4$=H, 1-naphthyl); 38% yield
Trioxane 23b3 (formula 23, $R_1$=$R_2$=Me, X=H, $R_3$, $R_4$=H, 1-naphthyl); 7% yield
Trioxane 23b4 (formula 23, $R_1$=$R_2$=Me, X=H, $R_3$, $R_4$=$CH_2$($CH_2$)$_4$—$CH_3$); 15% yield
Trioxane 23c1 (formula 23, $R_1$, $R_2$=H, Me; X=H, $R_3$, $R_4$=—$CH_2$—$CH_2$—$CH_2$—$CH_3$); 42% yield
Trioxane 23c2 (formula 23, $R_1$, $R_2$=H, Me; X=H, $R_3$, $R_4$=—$CH_2$—($CH_2$)$_3$—$CH_3$); 46% yield
Trioxane 23d1 (formula 23, $R_1$, $R_2$=H, Et; X=H, $R_3$, $R_4$=—$CH_2$—$CH_2$—$CH_2$—$CH_3$); 46% yield
Trioxane 23e2 (formula 23, $R_1$, $R_2$=H, n-pentyl; X=H, $R_3$, $R_4$=—$CH_2$—($CH_2$)$_3$—$CH_3$); 54% yield
Trioxane 23e3 (formula 23, $R_1$, $R_2$=H, n-pentyl; X=H, $R_3$, $R_4$=—$CH_2$—($CH_2$)$_4$—$CH_3$); 38% yield
Trioxane 23e4 (formula 23, $R_1$, $R_2$=H, n-pentyl; X=H, $R_3$, $R_4$=—$CH_2$—($CH_2$)$_5$—$CH_3$); 15% yield
Trioxane 23e5 (formula 23, $R_1$, $R_2$=H, n-pentyl; X=H, $R_3$, $R_4$=Me); 54% yield
Trioxane 23f1 (formula 23, $R_1$=$R_2$=H; X=OMe; $R_3$, $R_4$=—$CH_2$—$CH_2$—$CH_2$—$CH_3$); 27% yield
Trioxane 23f2 (formula 23, $R_1$=$R_2$=H; X=OMe; $R_3$, $R_4$=—$CH_2$—($CH_2$)$_3$—$CH_3$); 16% yield
Trioxane 23g1 (formula 23, $R_1$=$R_2$=Me; X=OMe; $R_3$, $R_4$=—$CH_2$—$CH_2$—$CH_2$—$CH_3$); 28% yield
Trioxane 24a2 (formula 24, $R_1$=$R_2$=H; $R_3$, $R_4$=—$CH_2$—($CH_2$)$_3$—$CH_3$); 41% yield
Trioxane 24a3 (formula 24, $R_1$=$R_2$=H; $R_3$, $R_4$=—$CH_2$—($CH_2$)$_4$—$CH_3$); 60% yield
Trioxane 24b3 (formula 24, $R_1$=$R_2$=Me; $R_3$, $R_4$=H, 1-naphthyl); 24% yield
Trioxane 25a (formula 25, $R_1$=$R_2$=H); 34% yield
Trioxane 25c (formula 25, $R_1$, $R_2$=H, Me); 39% yield
Trioxane 25d (formula 25, $R_1$, $R_2$=H, Et); 15% yield
Trioxane 25e (formula 25, $R_1$, $R_2$=H, n-pentyl); 35% yield
Trioxane 26a (formula 26, $R_1$, $R_2$=H); 23% yield
Trioxane 26b (formula 26, $R_1$, $R_2$=Me); 53% yield
Trioxane 27c (formula 27, $R_1$, $R_2$=H, Me); 39% yield
Trioxane 28b (formula 28, $R_1$, $R_2$=Me); 27% yield
Compound 31a2 (formula 31, $R_1$=$R_2$=X=H; $R_3$, $R_4$=—$CH_2$—$CH_2$—$CH_2$—$CH_3$; $R_5$=Et); 80% yield
Compound 31a3 (formula 31, $R_1$=$R_2$=X=H; $R_3$, $R_4$=—$CH_2$—$CH_2$—$CH_2$—$CH_3$; $R_5$=n-Pr); 78% yield
Compound 31a4 (formula 31, $R_1$=$R_2$=X=H; $R_3$, $R_4$=—$CH_2$—$CH_2$—$CH_2$—$CH_3$; $R_5$=n-hexyl); 75% yield
Compound 31a5 (formula 31, $R_1$=$R_2$=X=H; $R_3$, $R_4$=—$CH_2$—$CH_2$—$CH_2$—$CH_3$; $R_5$=phenyl); 42% yield
Compound 31a6 (formula 31, $R_1$=$R_2$=X=H; $R_3$, $R_4$=H, 1-naphthyl; $R_5$=$CH_3$); 36% yield
Compound 31b1 (formula 31, $R_1$=$R_2$=Me, X=H; $R_3$, $R_4$=H, 1-naphthyl; $R_5$=$CH_3$); 90% yield
Compound 32b1 (formula 32, $R_1$=$R_2$=Me; $R_3$, $R_4$=—$CH_2$—$CH_2$—$CH_2$—$CH_3$; $R_5$=Me); 89% yield
Compound 32b2 (formula 32, $R_1$=$R_2$=Me; $R_3$, $R_4$=—$CH_2$—($CH_2$)$_3$—$CH_3$; $R_5$=Me); 86% yield
Compound 32b3 (formula 32, $R_1$=$R_2$=Me; $R_3$, $R_4$=H, 1-naphthyl; $R_5$=Me); 73% yield
Compound 33a1 (formula 33, $R_1$=$R_2$=X=H; $R_5$=Me); 82% yield
Compound 33a2 (formula 33, $R_1$=$R_2$=X=H; $R_5$=Et); 76% yield
Compound 33a3 (formula 33, $R_1$=$R_2$=X=H; $R_5$=n-hexyl); 83% yield
Compound 34b (formula 34, $R_1$=$R_2$=Me; $R_5$=Me); 94% yield
Compound 35b3 (formula 35, $R_1$=$R_2$=Me; X=H; $R_5$=n-Pr); 57% yield
Compound 35b5 (formula 35, $R_1$=$R_2$=Me; X=H; $R_5$=n-hexyl); 95% yield
Compound 36b (formula 36, $R_1$=$R_2$=R=Me); 91% yield
Compound 37a1 (formula 37, $R_1$=$R_2$=X=H; $R_3$, $R_4$=—$CH_2$—$CH_2$—$CH_2$—$CH_3$); 87% yield
Compound 37a2 (formula 37, $R_1$=$R_2$=X=H; $R_3$, $R_4$=—$CH_2$—($CH_2$)$_3$—$CH_3$); 40% yield
Compound 37a3 (formula 37; $R_1$=$R_2$=X=H; $R_3$=$R_4$=Me); 70% yield
Compound 37a4 (formula 37; $R_1$=$R_2$=X=H; $R_3$=$R_4$=H, 1-naphthyl); 66% yield
Compound 37b2 (formula 37; $R_1$=$R_2$=Me; X=H; $R_3$, $R_4$=—$CH_2$—($CH_2$)$_3$—$CH_3$); 86% yield
Compound 37b3 (formula 37; $R_1$=$R_2$=Me; X=H; $R_3$, $R_4$=H, 1-naphthyl); 66% yield
Compound 37e1 (formula 37; $R_1$, $R_2$=H, n-pentyl; X=H; $R_3$, $R_4$=—$CH_2CH_2CH_2CH_3$); 79% yield
Compound 37f1 (formula 37; $R_1$=$R_2$=H; X=OMe; $R_3$, $R_4$=—$CH_2$—$CH_2$—$CH_2$—$CH_3$); 76% yield
Compound 38a2 (formula 38; $R_1$=$R_2$=H; $R_3$, $R_4$=—$CH_2$($CH_2$)$_3$—$CH_3$); 90%
Compound 38b1 (formula 38; $R_1$=$R_2$=Me; $R_3$, $R_4$=—$CH_2$—$CH_2$—$CH_2$—$CH_3$); 92% yield
Compound 38b2 (formula 38; $R_1$=$R_2$=Me; $R_3$, $R_4$=—$CH_2$($CH_2$)$_3$—$CH_3$); 88% yield
Compound 38b3 (formula 38; $R_1$=$R_2$=Me; $R_3$, $R_4$=H, 1-naphthyl); 87% yield
Compound 39a (formula 39; $R_1$=$R_2$=X=H); 97% yield
Compound 40b (formula 40; $R_1$=$R_2$=Me); 96% yield
Compound 41f (formula 41; $R_1$=$R_2$=H; X=OMe); 80% yield
Compound 41g (formula 41; $R_1$=$R_2$=Me, X=OMe); 80% yield
Compound 42a (formula 42; $R_1$=$R_2$=H); 91% yield Anti-malarial Activity The anti-malarial activity of the test compounds was evaluated in rodent using multidrug resistant strain of *Plasmodium yoelii* Nigeriensis in Swiss mice.

General Procedure

Random bred Swiss mice of either sex (20±2 gm) were inoculated intraperitoneally with $1\times10^5$ *P. yoelii* (MDR) parasites on day zero. The treatment with test compounds was administered to groups of 6 mice each at different dose levels ranging between 24–96 mg/kg/day. The trioxanes were dissolved in groundnut oil (or 50% sodium bicarbonate solutions in case of hemisuccinate derivatives) and were administered via intramuscular or oral route for 4 consecutive days (day 0–3).

Blood smears from experimental mice were observed on day 4 and 7, day 10 and thereafter at regular intervals till day 28 or death of the animal. The parasitaemia level on day 4 was compared with the vehicle control group and the percent suppression of parasitaemia in treated groups was calculated.

For determining the curative dose of a compound the treated mice were observed till day 28. The dose at which no parasitaemia develop during the observation period has been recorded as the curative dose. The anti-malarial data is summarized in Table 4.

TABLE 4

Anti-malarial activity of substituted trioxanes against multi drug resistance strain of *Plasmodium yoelii* Nigeriensis in Swiss mice

| Compd. No. | Route | Dose mg/kg | No. of animals | % Suppression on day 4 | Cured/Treated |
|---|---|---|---|---|---|
| 23a1 | im | 96 | 6 | 100 | 1/6 |
|  | im | 48 | 5 | 100 | 0/5 |
| 23a2 | im | 96 | 5 | 100 | 0/5 |
|  | im | 48 | 5 | 100 | 1/5 |
| 23a4 | im | 96 | 6 | 70 | 0/5 |
| 23b1 | im | 96 | 5 | 98 | 2/5 |
| 23b2 | im | 96 | 5 | 100 | 2/5 |
| 23c1 | im | 96 | 6 | 100 | 3/6 |
| 23c2 | im | 96 | 6 | 100 | 0/6 |
| 23e1 | im | 96 | 5 | 100 | 1/5 |
| 23e2 | im | 96 | 6 | 92 | 0/5 |
| 23f1 | im | 96 | 5 | 100 | 0/5 |
|  | im | 48 | 5 | 100 | 0/5 |
| 23f2 | im | 96 | 5 | 97 | 0/5 |
| 23g1 | im | 96 | 6 | 93 | 0/6 |
| 24a1 | im | 96 | 6 | 100 | 0/6 |
| 24a2 | im | 96 | 6 | 89 | 0/6 |
| 24a3 | im | 96 | 6 | 100 | 0/6 |
| 24b2 | im | 96 | 6 | 83 | 0/6 |
| 25a | im | 96 | 6 | 100 | 6/6 |
| 25c | im | 96 | 6 | 100 | 5/6 |
|  | im | 48 | 6 | 100 | 1/6 |
| 25e | im | 96 | 6 | 81 | 0/6 |
| 26a | im | 96 | 6 | 100 | — |
|  | im | 48 | 6 | 88 | — |
| 27a | im | 96 | 6 | 100 | 6/6 |
|  | im | 48 | 6 | 100 | 6/6 |
|  | im | 24 | 6 | 100 | 1/6 |
|  | oral | 96 | 6 | 100 | 2/6 |
|  | oral | 48 | 5 | 100 | 0/6 |
| 27b | oral | 96 | 6 | 100 | 6/6 |
|  | oral | 72 | 6 | 100 | 6/6 |
|  | oral | 48 | 6 | 100 | 1/6 |
|  | im | 96 | 6 | 100 | 6/6 |
|  | im | 72 | 6 | 100 | 6/6 |
|  | im | 48 | 6 | 100 | 5/6 |
| 27c | im | 96 | 6 | 100 | 6/6 |
|  | im | 48 | 6 | 100 | 3/6 |
| 27e | im | 96 | 5 | 84 | 0/6 |
|  | im | 48 | 6 | 15 | 0/6 |
| 27f | im | 96 | 6 | 100 | 6/6 |
|  | im | 48 | 6 | 100 | 1/6 |

TABLE 4-continued

Anti-malarial activity of substituted trioxanes against multi drug resistance strain of *Plasmodium yoelii* Nigeriensis in Swiss mice

| Compd. No. | Route | Dose mg/kg | No. of animals | % Suppression on day 4 | Cured/Treated |
|---|---|---|---|---|---|
| 27g | im | 96 | 6 | 92 | — |
|  | im | 48 | 6 | 85 | — |
| 28a | im | 96 | 5 | 100 | 5/5 |
|  | im | 48 | 5 | 100 | 3/5 |
| 28b | im | 96 | 6 | 96 | — |
|  | im | 48 | 6 | 66 | — |
| 31a1 | im | 96 | 6 | 100 | 6/6 |
|  | im | 64 | 5 | 100 | 1/5 |
|  | im | 48 | 6 | 100 | 2/6 |
| 31a2 | im | 96 | 6 | 97 | 0/6 |
|  | im | 48 | 6 | 47 | 0/6 |
| 31a3 | im | 96 | 6 | 36 | 0/6 |
|  | im | 48 | 6 | 26 | 0/6 |
| 31a4 | im | 96 | 6 | 22 | 0/6 |
|  | im | 48 | 6 | 22 | 0/6 |
| 31a5 | im | 96 | 6 | 57 | 0/6 |
|  | im | 48 | 6 | 41 | 0/6 |
| 31b2 | im | 96 | 6 | 20 | 0/6 |
|  | im | 96 | 6 | 75 | 0/6 |
| 33a1 | im | 96 | 6 | 99.5 | 0/6 |
|  | im | 48 | 6 | 96.8 | 0/6 |
| 33a2 | im | 96 | 6 | 52.5 | 0/6 |
|  | im | 48 | 6 | 61.6 | 0/6 |
| 33a3 | im | 96 | 6 | 0 | 0/6 |
|  | im | 48 | 6 | 14 | 0/6 |
| 35a1 | im | 96 | 6 | 100 | 6/6 |
|  | im | 48 | 6 | 99 | 0/6 |
|  | oral | 48 | 6 | 92 | 1/6 |
|  | im | 96 | 6 | 100 | 6/6 |
| 35b1 | oral | 96 | 6 | 100 | 1/6 |
|  | im | 96 | 5 | 99 | 1/5 |
| 35b2 | im | 96 | 5 | 94 | 0/6 |
|  | oral | 96 | 5 | 100 | 0/6 |
| 35b4 | im | 96 | 5 | 0 | 0/6 |
|  | oral | 96 | 5 | 35 | 0/6 |
| 35b5 | im | 96 | 5 | 67 | 0/6 |
|  | oral | 96 | 5 | 80 | 0/6 |
| 37a1 | im | 128 | 6 | 0 | 0/6 |
| 37a2 | im | 128 | 6 | 91.6 | 0/6 |
| 37a3 | im | 128 | 6 | 83 | 0/6 |
|  | im | 64 | 5 | 53 | 0/5 |
| 37b1 | im | 96 | 6 | — | 1/6 |
|  | im | 48 | 6 | — | 2/6 |
| 37e1 | im | 96 | 6 | 100 | 1/6 |
|  | oral | 96 | 6 | 82 | 0/6 |
| 38a1 | im | 96 | 6 | 82 | 0/6 |
|  | im | 48 | 6 | 62 | 0/6 |
| 38a2 | im | 96 | 6 | 59 | 0/6 |
|  | im | 48 | 6 | 55 | 0/6 |
| 39a | im | 96 | 5 | 94 | 0/5 |
|  | im | 48 | 5 | 93 | 1/5 |
| 41a | im | 64 | 6 | 100 | 6/6 |
|  | im | 48 | 6 | 100 | 6/6 |
|  | oral | 96 | 6 | 100 | 6/6 |
|  | oral | 48 | 6 | 100 | 0/6 |
| 41b | im | 64 | 6 | 100 | 6/6 |
|  | im | 72 | 6 | 100 | 6/6 |
|  | im | 48 | 6 | 100 | 5/6 |
|  | im | 24 | 6 | 100 | 3/6 |
|  | oral | 96 | 6 | 100 | 6/6 |
|  | oral | 96 | 6 | 100 | 6/6 |
|  | oral | 48 | 6 | 100 | 2/6 |
| 41e | im | 96 | 6 | 100 | 0/6 |
|  | oral | 96 | 6 | 97 | 0/6 |
| 42a | im | 96 | 5 | 100 | 2/5 |
|  | im | 48 | 5 | 78 | 0/5 |
| 42b | im | 96 | 6 | 100 | 0/6 |
|  | oral | 96 | 6 | 96 | 0/6 |

Trioxanes 27a and 27b and their hemisuccinates 41a and 41b were evaluated for blood schizontocidal activity against

*Plasmodium cynomolgi* and *Plasmodium knowlesi* in Rhesus monkeys using the following protocol:

For activity against *P. cynomolgi*, rhesus monkeys were inoculated intravenously with $1 \times 10^5$ parasitized RBC and the treatment was initiated when the parasitaemia level reached above 0.5%. For activity against *P. knowlesi* the rhesus monkeys were inoculated intravenously with $1 \times 10^4$ parasitized RBC and the treatment was initiated at 0.1% parasitaemia level.

Compounds 27a and 27b were dissolved in groundnut oil and administered in various regimens for 3–5 days via oral or intramuscular (im) routes. Hemisuccinates 41a and 41b were dissolved in 5% bicarbonate solution and administered similarly by oral, im or iv routes.

The blood smears from the treated monkeys were examined once daily to record parasitaemia clearance time and subsequent recurrence of parasitaemia. The animals in which no recrudescence was observed up to day 60 were recorded as cured. The anti-malarial data are summarized in Table 5 and Table 6.

TABLE 5

Anti-malarial activity of trioxanes against
Plasmodium cynomolgi in rhesus monkey model

| Compound | Route | Dose mg/ kg × days | Regimen | Time for complete clearance of parasitaemia (hr) | Cure rate |
|---|---|---|---|---|---|
| 27a | im | 10.0 × 4 | Divided | 48 | 2/2 |
|  | im | 10.0 × 4 | Single | 48 | 3/4 |
|  | im | 7.5 × 4 | Single | 48 | 1/2 |
|  | im | 5.0 × 4 | Divided | 48–72 | 1/2 |
|  | oral | 20.0 × 5 | Divided | 72 | 2/2 |
|  | oral | 20.5 × 5 | Divided | 48 | 3/3 |
|  | oral | 15.0 × 5 | Divided | 48 | 3/3 |
|  | oral | 10.0 × 5 | Divided | 48 | 0/2 |
| 27b | im | 15.0 × 4 | Divided | 48 | 2/2 |
|  | im | 10.0 × 4 | Divided | 72 | 2/2 |
|  | oral | 20.0 × 5 | Divided | 48 | 2/2 |
|  | oral | 20.0 × 5 | Divided | 72 | 2/2 |
|  | oral | 15.0 × 5 | Divided | 72 | 2/2 |
| 41a | im | 10.0 × 4 | Divided | 48 | 4/4 |
|  | im | 10.0 × 4 | Single | 48 | 2/2 |
|  | im | 7.5 × 4 | Single | 48 | 1/2 |
|  | oral | 20.0 × 5 | Divided | 48 | 3/3 |
|  | oral | 20.0 × 4 | Divided | 48 | 2/2 |
|  | oral | 15.0 × 5 | Divided | 48 | 0/2 |
| 41b | iv | 10.0 × 4 | Divided | 48 | 2/2 |
|  | im | 10.0 × 4 | Divided | 48 | 2/2 |
|  | im | 10.0 × 4 | Single | 48–72 | 0/2 |
|  | oral | 20.0 × 5 | Divided | 48–72 | 2/2 |
|  | oral | 10.0 × 5 | Divided | 96 | 0/2 |
|  | oral | 20.0 × 1 + 10.0 × 4 | Divided | 48–72 | 5/5 |

TABLE 6

Anti-malarial activity of trioxanes against
*P. knowlesi* in rhesus monkey model

| Compound | Route | Dose mg/ kg × days | Regimen | Time for complete clearance of parasitaemia (hr) | Cure rate |
|---|---|---|---|---|---|
| 27a | im | 20.0 × 4 | Divided | 48 | 2/2 |
|  | im | 15.0 × 4 | Divided | 48 | 2/2 |
|  | im | 10.0 × 4 | Divided | 48 | 0/2 |
|  | im | 5.0 × 4 | Divided | 72 | 0/2 |
|  | oral | 15.0 × 4 | Divided | 48–72 | 2/2 |
| 41a | im | 20.0 × 4 | Divided | 48 | 2/2 |

TABLE 6-continued

Anti-malarial activity of trioxanes against
*P. knowlesi* in rhesus monkey model

| Compound | Route | Dose mg/ kg × days | Regimen | Time for complete clearance of parasitaemia (hr) | Cure rate |
|---|---|---|---|---|---|
|  | im | 15.0 × 4 | Divided | 48 | 1/2 |
|  | oral | 30.0 × 4 | Divided | 48 | 1/2 |
|  | oral | 15.0 × 4 | Divided | 48 | 0/2 |

Gametocytocidal Activity

Compounds 27a and 41a were also tested for gametocytocidal activity according to the following protocol:

Different batches of 3 to 4 days old naïve *Anopheles stephensis* mosquitoes are allowed to engorge blood from gametocyte carrying infected host (rhesus monkey infected with *P. cytnomolgi* or hamster infected with *P. yoelii*) at different time intervals prior to and after administration with a single dose of the test compound. The blood-fed mosquitoes were maintained for the next 7–10 days in an insectorium to allow development of oocysts. A comparison of mosquito infectivity rate and oocyst numbers in pre-treatment versus post-treatment provided index for gametocytocidal potential of the test agent.

Compounds 27a and 41a showed complete loss of infectivity in mosquito batches fed 24 h. post-treatment with 50 mg/kg (im, single dose) in *P. yoelii* model and 20 mg/kg (im, single dose) or 30 mg/kg (oral, single dose) in *P. cynomolgi* model.

What is claimed is:

1. Novel substituted 1,2,4-trioxanes of formula 1,

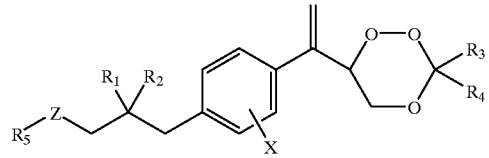

wherein $R_1$ and $R_2$ are selected from the group consisting of a hydrogen and a $C_{1-11}$ alkyl group; $R_3$ and $R_4$ are selected from the group consisting of a hydrogen, a $C_{1-11}$ alkyl group, and a $C_{3-10}$ aryl group; $R_5$ is selected from the group consisting of a hydrogen, a $C_{1-11}$ alkyl group, a $C_{3-10}$ aryl group, a $C_{1-2}CO_2H$ carboxyalkyl group; Z is O or OCO; and X is hydrogen or a lower alkoxy group having 1 to 6 carbons.

2. Novel trioxanes as claimed in claim 1, wherein said compounds have the structural formulae 23a1–23a13, 23b1–23b4, 23c1–23c2, 23d1, 23e1–23e5, 23f1–23f2, and 23g1 as shown below:

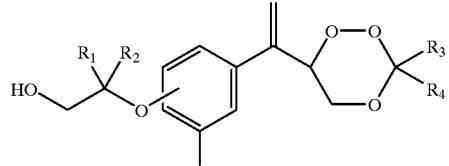

wherein,

23a1 $R_1$, $R_2$=H, H; X=H; $R_3$, $R_4$=CH$_2$CH$_2$CH$_2$CH$_3$
23a2 $R_1$, $R_2$=H, H; X=H; $R_3$, $R_4$=CH$_2$CH$_2$CH$_2$CH$_2$CH$_3$
23a3 $R_1$, $R_2$=H, H; X=H; $R_3$, $R_4$=Me, Me
23a4 $R_1$, $R_2$=H, H; X=H; $R_3$, $R_4$=Me, Et
23a5 $R_1$, $R_2$=H, H; X=H; $R_3$, $R_4$=Me, CH$_2$CH$_2$CH$_3$
23a6 $R_1$, $R_2$=H, H; X=H; $R_3$, $R_4$=Me, CH$_2$CHMe$_2$
23a7 $R_1$, $R_2$=H, H; X=H; $R_3$, $R_4$=n-propyl, n-propyl
23a8 $R_1$, $R_2$=H, H; X=H; $R_3$, $R_4$=n-butyl, n-butyl
23a9 $R_1$, $R_2$=H, H; X=H; $R_3$, $R_4$=n-pentyl, n-pentyl
23a10 $R_1$, $R_2$=H, H; X=H; $R_3$, $R_4$=—CH$_2$—(CH$_2$)$_9$—CH$_3$
23a11 $R_1$, $R_2$=H, H; X=H; $R_3$, $R_4$=CH$_2$CH$_2$—CO—CH$_2$—CH$_3$
23a12 $R_1$, $R_2$=H, H; X=H; $R_3$, $R_4$=H, phenyl
23a13 $R_1$, $R_2$=H, H; X=H; $R_3$, $R_4$=H, 1-naphthyl
23b1 $R_1$, $R_2$=Me, Me; X=H; $R_3$, $R_4$=CH$_2$CH$_2$CH$_2$CH$_3$
23b2 $R_1$, $R_2$=Me, Me; X=H; $R_3$, $R_4$=CH$_2$CH$_2$CH$_2$CH$_2$CH$_3$
23b3 $R_1$, $R_2$=Me, Me; X=H; $R_3$, $R_4$=H, 1-naphthyl
23b4 $R_1$, $R_2$=Me, Me; X=H; $R_4$=—CH$_2$—(CH$_2$)$_4$—CH$_3$
23c1 $R_1$, $R_2$=H, Me; X=H; $R_3$, $R_4$=CH$_2$CH$_2$CH$_2$CH$_3$
23c2 $R_1$, $R_2$=H, Me; X=H; $R_3$, $R_4$=CH$_2$CH$_2$CH$_2$CH$_2$CH$_3$
23d1 $R_1$, $R_2$=H, Et; X=H; $R_3$, $R_4$=CH$_2$CH$_2$CH$_2$CH$_3$
23e1 $R_1$, $R_2$=H, n-pentyl; X=H; $R_3$, $R_4$=CH$_2$CH$_2$CH$_2$CH$_3$
23e2 $R_1$, $R_2$=H, n-pentyl; X=H; $R_3$, $R_4$=CH$_2$CH$_2$CH$_2$CH$_3$
23e3 $R_1$, $R_2$=H, n-pentyl; X=H; $R_3$, $R_4$=CH$_2$(CH$_2$)$_4$CH$_3$
23e4 $R_1$, $R_2$=H, n-pentyl; X=H; $R_3$, $R_4$=CH$_2$(CH$_2$)$_5$CH$_3$
23e5 $R_1$, $R_2$=H, n-pentyl; X=H; $R_3$, $R_4$=Me, Me
23f1 $R_1$, $R_2$=H, H; X=OMe; $R_3$, $R_4$=CH$_2$CH$_2$CH$_2$CH$_3$
23f2 $R_1$, $R_2$=H, H; X=OMe; $R_3$, $R_4$=CH$_2$—(CH$_2$)$_3$—CH$_3$
23g1 $R_1$, $R_2$=Me, Me; X=OMe; $R_3$, $R_4$=CH$_2$CH$_2$CH$_2$CH$_3$.

3. Novel trioxanes as claimed in claim 1, wherein said compounds have the structural formulae 24a1–24a3 and 24b1–24b3 as shown below:

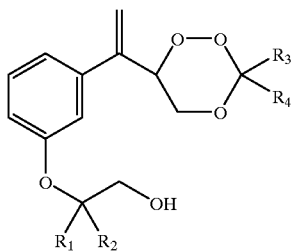

wherein,

24a1 $R_1$, $R_2$=H, H; $R_3$, $R_4$=CH$_2$CH$_2$CH$_2$CH$_3$
24a2 $R_1$, $R_2$=H, H; $R_3$, $R_4$=CH$_2$(CH$_2$)$_3$—CH$_3$
24a3 $R_1$, $R_2$=H, H; $R_3$, $R_4$=CH$_2$(CH$_2$)$_4$—CH$_3$
24b1 $R_1$, $R_2$=Me, Me; $R_3$, $R_4$=CH$_2$CH$_2$CH$_2$CH$_3$
24b2 $R_1$, $R_2$=Me, Me; $R_3$, $R_4$=CH$_2$CH$_2$CH$_2$CH$_2$CH$_3$
24b3 $R_1$, $R_2$=Me, Me; $R_3$, $R_4$=H, 1-naphthyl.

4. Novel trioxanes as claimed in claim 1, wherein said compounds have the structural formulae 25a, 25c, 25d, and 25e as shown below:

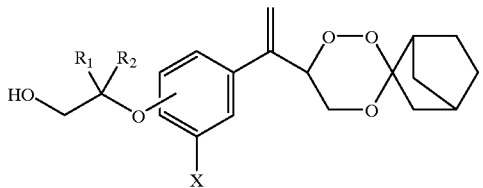

wherein,

25a $R_1$, $R_2$=H, H; X=H
25c $R_1$, $R_2$=H, Me; X=H
25d $R_1$, $R_2$=H, Et; X=H;
25e $R_1$, $R_2$=H, n-phenyl; X=H.

5. Novel trioxanes as claimed in claim 1, wherein said compounds have the structural formulae 26a and 26b as shown below:

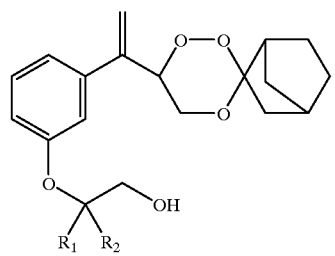

wherein,

26a $R_1$, $R_2$=H, H
26b $R_1$, $R_2$=Me, Me.

6. Novel trioxanes as claimed in claim 1, wherein said compounds have the structural formulae 27a, 27b, 27c, 27d, 27e, 27f, and 27g as shown below:

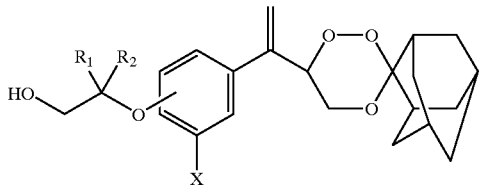

wherein,

27a $R_1$, $R_2$=H, H; X=H
27b $R_1$, $R_2$=Me, Me; X=H
27c $R_1$, $R_2$=He, Me; X=H
27d $R_1$, $R_2$=H, Et; X=H
27e $R_1$, $R_2$=H, n-pentyl; X=H
27f $R_1$, $R_2$=H, H; X=OMe
27g $R_1$, $R_2$=Me, Me; X=OMe.

7. Novel trioxanes as claimed in claim 1, wherein said compounds have the structural formulae 28a and 28b as shown below:

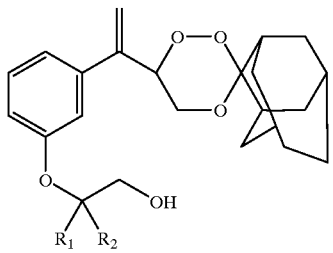

wherein,

28a $R_1$, $R_2$=H, H
28b $R_1$, $R_2$=Me, Me.

8. Novel trioxanes as claimed in claim 1, wherein said compounds have the structural formulae 31a–31a6 and 31b1 as shown below:

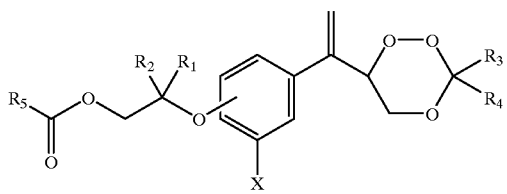

wherein,

31a1 $R_1$, $R_2$=H, H; X=H; $R_3$, $R_4$=$CH_2CH_2CH_2CH_3$; $R_5$=$CH_3$
31a2 $R_1$, $R_2$=H, H; X=H; $R_3$, $R_4$=$CH_2CH_2CH_2CH_3$; $R_5$=Et
31a3 $R_1$, $R_2$=H, H; X=H; $R_3$, $R_4$=$CH_2CH_2CH_2CH_3$; $R_5$=n-propyl
31a4 $R_1$, $R_2$=H, H; X=H; $R_3$, $R_4$=$CH_2CH_2CH_2CH_3$; $R_5$=n-hexyl
31a5 $R_1$, $R_2$=H, H; X=H; $R_3$, $R_4$=$CH_2CH_2CH_2CH_3$; $R_5$=Phenyl
31a6 $R_1$, $R_2$=H, H; X=H; $R_3$, $R_4$=H, 1-naphthyl; $R_5$=$CH_3$
31b1 $R_1$, $R_2$=Me, Me; X=H; $R_3$, $R_4$=H, 1-naphthyl; $R_5$=Me.

9. Novel trioxanes as claimed in claim 1, wherein said compounds have the structural formulae 32b1–31b3 as shown below:

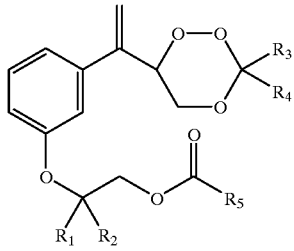

wherein,

32b1 $R_1$, $R_2$=Me, Me; X=H; $R_3$, $R_4$=$CH_2CH_2CH_2CH_3$; $R_5$=Me
32b2 $R_1$, $R_2$=Me, Me; X=H; $R_3$, $R_4$=$CH_2CH_2CH_2CH_3$; $R_5$=Me
32b3 $R_1$, $R_2$=Me, Me; X=H; $R_3$, $R_4$=H, 1-naphthyl; $R_5$=Me.

10. Novel trioxanes as claimed in claim 1, wherein said compounds have the structural formulae 33a1–33a3 as shown below:

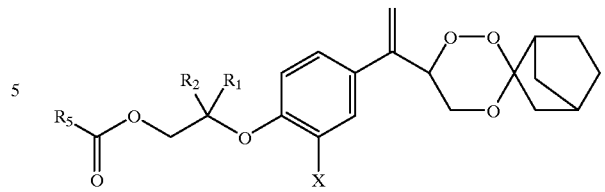

wherein,

33a1 $R_1$, $R_2$=H, H; X=H; $R_5$=Me
33a2 $R_1$, $R_2$=H, H; X=H; $R_5$=Et
33a3 $R_1$, $R_2$=H, H; X=H; $R_5$=n-hexyl.

11. Novel trioxanes as claimed in claim 1, wherein said compound has the structural formula 34b as shown below:

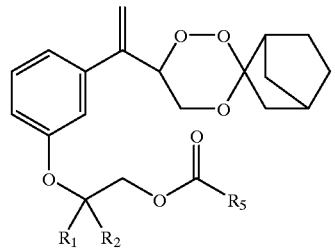

wherein,

34b $R_1$, $R_2$=Me, Me; X=H; $R_5$=Me.

12. Novel trioxanes as claimed in claim 1, wherein said compounds have the structural formulae 35a1, 35b1–35b5 as shown below:

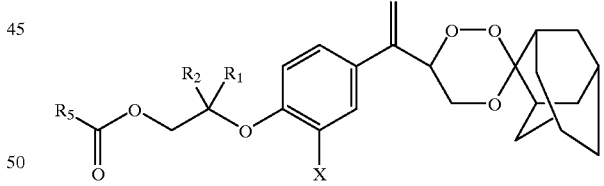

wherein,

35a1 $R_1$, $R_2$=H, H; X=H; $R_5$=Me
35b1 $R_1$, $R_2$=Me, Me; X=H; $R_5$=Me
35b2 $R_1$, $R_2$=Me, Me; X=H; $R_5$=Et
35b3 $R_1$, $R_2$=Me, Me; X=H; $R_5$=n-propyl
35b4 $R_1$, $R_2$=Me, Me; X=H; $R_5$=n-pentyl
35b5 $R_1$, $R_2$=Me, Me; X=H; $R_3$, $R_5$=n-hexyl.

13. Novel trioxanes as claimed in claim 1, wherein said compound has the structural formula 36b as shown below:

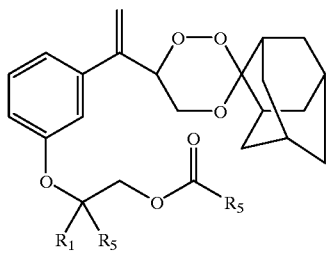

wherein,

36b $R_1$, $R_2$=Me, Me; X=H; $R_5$=Me.

14. Novel trioxanes as claimed in claim 1, wherein said compounds have the structural formulae 37a1–37a4, 37b1–37b3, 37e1, and 37f1 as shown below:

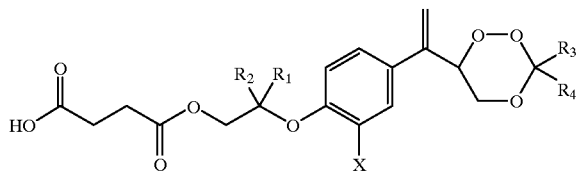

wherein,

37a1 $R_1$, $R_2$=H, H; X=H; $R_3$, $R_4$=$CH_2CH_2CH_2CH_2CH_3$
37a2 $R_1$, $R_2$=H, H; X=H; $R_3$, $R_4$=$CH_2CH_2CH_2CH_2CH_3$
37a3 $R_1$, $R_2$=H, H; X=H; $R_3$, $R_4$=Me, Me
37a4 $R_1$, $R_2$=H, H; X=H; $R_3$, $R_4$=H, 1-naphthyl
37b1 $R_1$, $R_2$=Me, Me; X=H; $R_3$, $R_4$=$CH_2CH_2CH_2CH_3$
37b2 $R_1$, $R_2$=Me, Me; X=H; $R_3$, $R_4$=$CH_2CH_2CH_2CH_3$
37b3 $R_1$, $R_2$=Me, Me; X=H; $R_3$, $R_4$=H, 1-naphthyl
37e1 $R_1$, $R_2$=H, n-pentyl; X=H; $R_3$, $R_4$=$CH_2CH_2CH_2CH_3$
37f1 $R_1$, $R_2$=H, H; X=OMe; $R_3$, $R_4$=$CH_2CH_2CH_2CH_3$.

15. Novel trioxanes as claimed in claim 1, wherein said compounds have the structural formulae 38a1–38a2 and 38b1–38b3 as shown below:

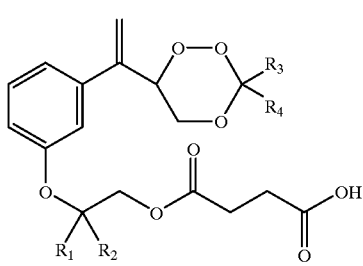

wherein,

38a1 $R_1$, $R_2$=H, H; $R_3$, $R_4$=$CH_2CH_2CH_2CH_3$
38a2 $R_1$, $R_2$=H, H; $R_3$, $R_4$=$CH_2CH_2CH_2CH_2CH_3$
38b1 $R_1$, $R_2$=Me, Me; $R_3$, $R_4$=$CH_2CH_2CH_2CH_3$
38b2 $R_1$, $R_2$=Me, Me; $R_3$, $R_4$=$CH_2CH_2CH_2CH_2CH_3$
38b3 $R_1$, $R_2$=Me, Me; $R_3$, $R_4$=H, 1-naphthyl.

16. Novel trioxanes as claimed in claim 1, wherein said compound has the structural formula 39a as shown below:

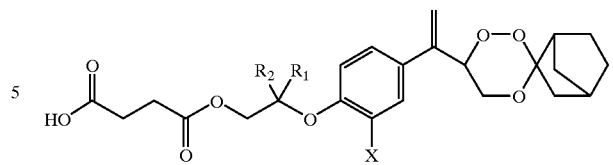

wherein,

39a $R_1$, $R_2$=H, H; X=H.

17. Novel trioxanes as claimed in claim 1, wherein said compound has the structural formula 40b as shown below:

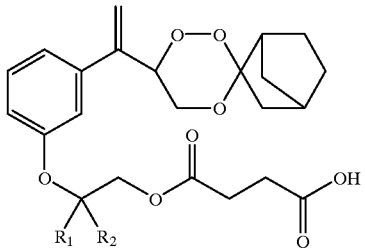

wherein

40b $R_1$, $R_2$=Me, Me.

18. Novel trioxanes as claimed in claim 1, wherein said compounds have the structural formulae, 41a, 41b, 41e, 41f, and 41g as shown below:

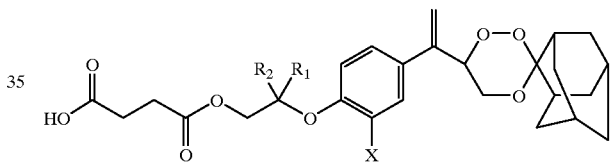

wherein,

41a $R_1$, $R_2$=H, H; X=H
41b $R_1$, $R_2$=Me, Me; X=H
41e $R_1$, $R_2$=H, n-pentyl; X=H
41f $R_1$, $R_2$=H, H; X=OMe
41g $R_1$, $R_2$=Me, Me; X=OMe.

19. Novel trioxanes as claimed in claim 1, wherein said compounds have the structural formulae 42a and 42b as shown below:

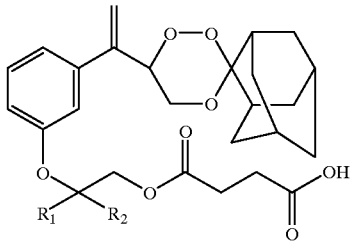

wherein,

42a $R_1$, $R_2$=H, H
42b $R_1$, $R_2$=Me, Me.

20. A process for the preparation of novel substituted 1,2,4-trioxanes and their esters of general formula 1, which comprises reacting hydroxyacetophenones of formula 2 wherein, X represents hydrogen or a lower alkoxy having 1 to 6 carbons, with α-haloesters of formula 3 wherein $R_1$ and $R_2$ are selected from the group consisting of a hydrogen, a $C_{1-11}$ alkyl group and Y represents a halogen, in the presence of a base optionally in an organic solvent at a temperature in the range of room temperature to refluxing temperature to give ketoesters of general formula 4, wherein $R_1$, $R_2$ and X have the same meaning as above; reacting ketoesters of general formula 4 under Reformatsky condition in an aprotic organic solvent in the temperature range of room temperature to refluxing temperature to give β-hydroxyesters of general formula 5, wherein $R_1$, $R_2$ and X have the same meaning as above, dehydrating β-hydroxyesters of formula 5 using a catalyst in an organic solvent at a temperature in the range of room temperature to refluxing temperature to give α,β-unsaturated esters of general formula 6, wherein $R_1$, $R_2$ and X have the same meaning as above; reducing α,β-unsaturated esters of general formula 6 with a complex metal hydride in an ether solvent at a temperature in the range of 0° C. to room temperature to give allylic alcohols of formula 7 wherein $R_1$, $R_2$ and X have the same meaning as above; oxygenation of allylic alcohols of formula 7 in the presence of a sensitizer in an organic solvent at a temperature in the range of −10° C. to room temperature to give β-hydroxyhydroperoxides of general formula 8 wherein $R_1$, $R_2$ and X have the same meaning as above; isolating and then reacting or reacting in situ β-hydroxyhydroperoxides of formula 8 with compounds containing an aldehyde or ketone group in the presence of an acid catalyst in an organic solvent at a temperature in the range of 0° C. to room temperature to give hydroxy-functionalized 1,2,4-trioxanes of general formula 1, wherein $R_1$, $R_2$ and X have the same meaning as above, $R_3$ and $R_4$ are selected from the group consisting of a hydrogen, a $C_{1-11}$ alkyl group, a $C_{3-10}$ aryl group, $R_5$ is H; and Z is O; reacting hydroxy-functionalized trioxanes of general formula 1, wherein $R_5$ is H and Z is O with an acid chloride or anhydrides in the presence of a base in an organic solvent at a temperature in the range of 0° C. to room temperature to give trioxane esters of general formula 1, wherein $R_1$, $R_2$, $R_3$, $R_4$ and X have the same meaning as above, $R_5$ is selected from the group consisting of a $C_{1-11}$ alkyl group, a $C_{3-10}$ aryl group, a $C_{1-2}CO_2H$ carboxyalkyl group; and Z is OCO.

21. A process as claimed in claim 20, wherein the substituted acetophenones of formula 2 are reacted with α-haloesters of formula 3 in the presence of a base selected from the group consisting of $KaHCO_3$, $Na_2CO_3$, and $K_2CO_3$, and in an organic solvent selected from the group consisting of acetone, DMSO, and DMF.

22. A process as claimed in claim 20 wherein, Reformatsky reaction is carried out by reacting ketoesters of formula 4 with ethyl bromoacetate and Zn in an aprotic organic solvent selected from the group consisting of benzene, diethylether, and THF.

23. A process as claimed in claim 20 wherein dehydration of β-hydroxyesters of formula 5 is effected in a hydrocarbon solvent selected from the group consisting of benzene, toluene, and $CH_2Cl_2$, using a catalyst selected from the group consisting of $I_2$, $P_2O_5$, p-toluene-sulfonic acid, and an acidic resin.

24. A process as claimed in claim 20 wherein the reduction of esters of formula 6 with $LiAlH_4$ is carried out in an ether solvent selected from the group consisting of diethyl ether and THF.

25. A process as claimed in claim 20 wherein the oxygenation is effected by photooxygenation of allylic alcohols of formula 7 in an organic solvent selected from the group consisting of acetone, $CH_3CN$, $CH_2Cl_2$, methanol, and ethanol, using a dye sensitizer selected from the group consisting of methylene blue, Rose Bengal, and tetraphenyl porphine.

26. A process as claimed in claim 20 wherein condensation of β-hydroxyhydroperoxides of formula 8 with aldehydes and ketones of formulae 21–22 is done in an organic solvent selected from the group consisting of $CH_2Cl_2$, $CHCl_3$, benzene, and $CH_3CN$, using an acid catalyst selected from the group consisting of HCl, $H_2SO_4$, p-toluene-sulfonic acid, $BF_3OEt_2$, and acidic resin.

27. A process as claimed in claim 20 wherein esterification of hydroxy-functionalized trioxanes of formulae 23–28 with acid chlorides of formula 29 or an acid anhydride of formula 30 is done in an organic solvent selected from the group consisting of $CH_2Cl_2$, $CHCl_3$, THF, and $CH_3CN$ in the presence of a base selected from the group consisting of $Et_3N$, pyridine, and dimethylaminopyridine.

28. A process as claimed in claim 20 wherein hemisuccinate derivatives of formulae 37–42 are prepared in an organic solvent selected from the group consisting of $CH_2Cl_2$, $CHCl_3$, $CH_3CN$, toluene, and THF, in the presence of a base selected from the group consisting of $Et_3N$, pyridine, and dimethylaminopyridine.

29. A process as claimed in claim 20 wherein the compounds containing aldehyde and ketonic groups are of formulae 21–22 wherein $R_3$ and $R_4$ are selected from the group consisting of a hydrogen, a $C_{1-11}$ alkyl group, a $C_{3-10}$ aryl group, and an araalkyl group, wherein said araalkyl is selected from the group consisting of said alkyl group and said aryl group.

30. A process as claimed in claim 20 wherein acid chlorides and acid anhydrides used have the formulae 29 and 30 wherein $R_5$ is selected from the group consisting of a $C_{1-11}$ alkyl group and a $C_{3-10}$ aryl group.

* * * * *